US012539238B2

(12) United States Patent
Nakamura

(10) Patent No.: US 12,539,238 B2
(45) Date of Patent: Feb. 3, 2026

(54) DISPOSABLE WEARABLE ARTICLE

(71) Applicant: DAIO PAPER CORPORATION, Ehime (JP)

(72) Inventor: Wataru Nakamura, Ehime (JP)

(73) Assignee: Daio Paper Corporation, Ehime (JP)

( * ) Notice: Subject to any disclaimer, the term of this patent is extended or adjusted under 35 U.S.C. 154(b) by 493 days.

(21) Appl. No.: 17/997,452

(22) PCT Filed: May 20, 2021

(86) PCT No.: PCT/JP2021/019189

§ 371 (c)(1),
(2) Date: Oct. 28, 2022

(87) PCT Pub. No.: WO2021/241396

PCT Pub. Date: Dec. 2, 2021

(65) Prior Publication Data

US 2023/0301845 A1 Sep. 28, 2023

(30) Foreign Application Priority Data

May 29, 2020 (JP) ................................ 2020-094371

(51) Int. Cl.
*A61F 13/511* (2006.01)
*A61F 13/15* (2006.01)

(52) U.S. Cl.
CPC .................. *A61F 13/51113* (2013.01); *A61F 2013/15447* (2013.01); *A61F 2013/51117* (2013.01)

(58) Field of Classification Search
CPC ...... A61F 13/51113; A61F 2013/15447; A61F 2013/51117; A61F 13/51121
See application file for complete search history.

(56) References Cited

U.S. PATENT DOCUMENTS 6,217,890 B1 * 4/2001 Paul ........................ A61L 15/48 604/378
6,296,862 B1 * 10/2001 Paul ........................ A61L 15/46 604/367
6,498,284 B1 * 12/2002 Roe ......................... A61L 15/20 604/378
(Continued)

FOREIGN PATENT DOCUMENTS

CN 208799412 U 4/2019
EP 0692263 A2 1/1996
(Continued)

OTHER PUBLICATIONS

International Search Report for PCT/JP2021/019189, dated Aug. 3, 2021.
(Continued)

*Primary Examiner* — Susan S Su
*Assistant Examiner* — Ted Yang
(74) *Attorney, Agent, or Firm* — Andrus Intellectual Property Law, LLP

(57) ABSTRACT

A disposable wearable article has a top sheet having a skin-touching region that is brought into contact with skin of a wearer, in which the top sheet is made from nonwoven fabric having a fineness of 1 to 3 dtex, and a basis weight of 10 to 30 g/m$^2$, and in which the skin-touching region has a glycerin-bearing zone bearing 0.7 to 2.7 g/m$^2$ of glycerin.

8 Claims, 16 Drawing Sheets

(56) References Cited

U.S. PATENT DOCUMENTS

| | | | | |
|---|---|---|---|---|
| 6,533,765 | B1 | 3/2003 | Blaney et al. | |
| 2002/0120241 | A1* | 8/2002 | Tyrrell | A61L 15/42 424/443 |
| 2002/0120242 | A1* | 8/2002 | Tyrrell | A61L 15/40 424/443 |
| 2002/0128615 | A1* | 9/2002 | Tyrrell | A61K 8/732 424/443 |
| 2002/0136755 | A1* | 9/2002 | Tyrrell | A61F 13/8405 424/769 |
| 2003/0130635 | A1* | 7/2003 | Tate | A61L 15/34 604/385.01 |
| 2003/0130636 | A1* | 7/2003 | Brock | A61F 13/8405 604/385.01 |
| 2003/0171728 | A1* | 9/2003 | Heyn | A61F 13/534 604/378 |
| 2003/0206979 | A1* | 11/2003 | Dvoracek | A61F 13/8405 424/766 |
| 2005/0142093 | A1* | 6/2005 | Skover | A61Q 19/08 601/84 |
| 2008/0286224 | A1 | 11/2008 | Vega et al. | |
| 2008/0287896 | A1 | 11/2008 | Vega et al. | |
| 2015/0209468 | A1* | 7/2015 | Aviles | C12N 1/20 424/447 |
| 2016/0184245 | A1* | 6/2016 | Eberting | A61K 8/41 514/170 |
| 2018/0042777 | A1* | 2/2018 | Dalal | A61F 13/15203 |
| 2018/0116951 | A1* | 5/2018 | Nistor | A61P 17/00 |
| 2018/0185449 | A1* | 7/2018 | Zoumalan | G07C 13/00 |
| 2019/0290575 | A1* | 9/2019 | Norman | A61Q 19/02 |
| 2019/0343856 | A1* | 11/2019 | Wagner | A61K 31/16 |
| 2021/0093537 | A1* | 4/2021 | Mondon | A61Q 19/00 |
| 2022/0202667 | A1* | 6/2022 | Ito | A61K 8/99 |

FOREIGN PATENT DOCUMENTS

| | | | |
|---|---|---|---|
| JP | H08252175 | A | 2/1996 |
| JP | 2002509457 | A | 3/2002 |
| JP | 2003-526468 | | 9/2003 |
| JP | 2004255165 | A | 9/2004 |
| JP | 2010526629 | A | 8/2010 |
| JP | 2010526630 | A | 8/2010 |
| JP | 2013-066598 | | 4/2013 |
| JP | 2014198175 | A | 10/2014 |
| JP | 2019170534 | A | 10/2019 |
| WO | 2013038965 | A1 | 3/2013 |

OTHER PUBLICATIONS

Office Action for CN Patent Appl. No. 202180030465.X, dated Jul. 22, 2025.

* cited by examiner

[FIG.1]
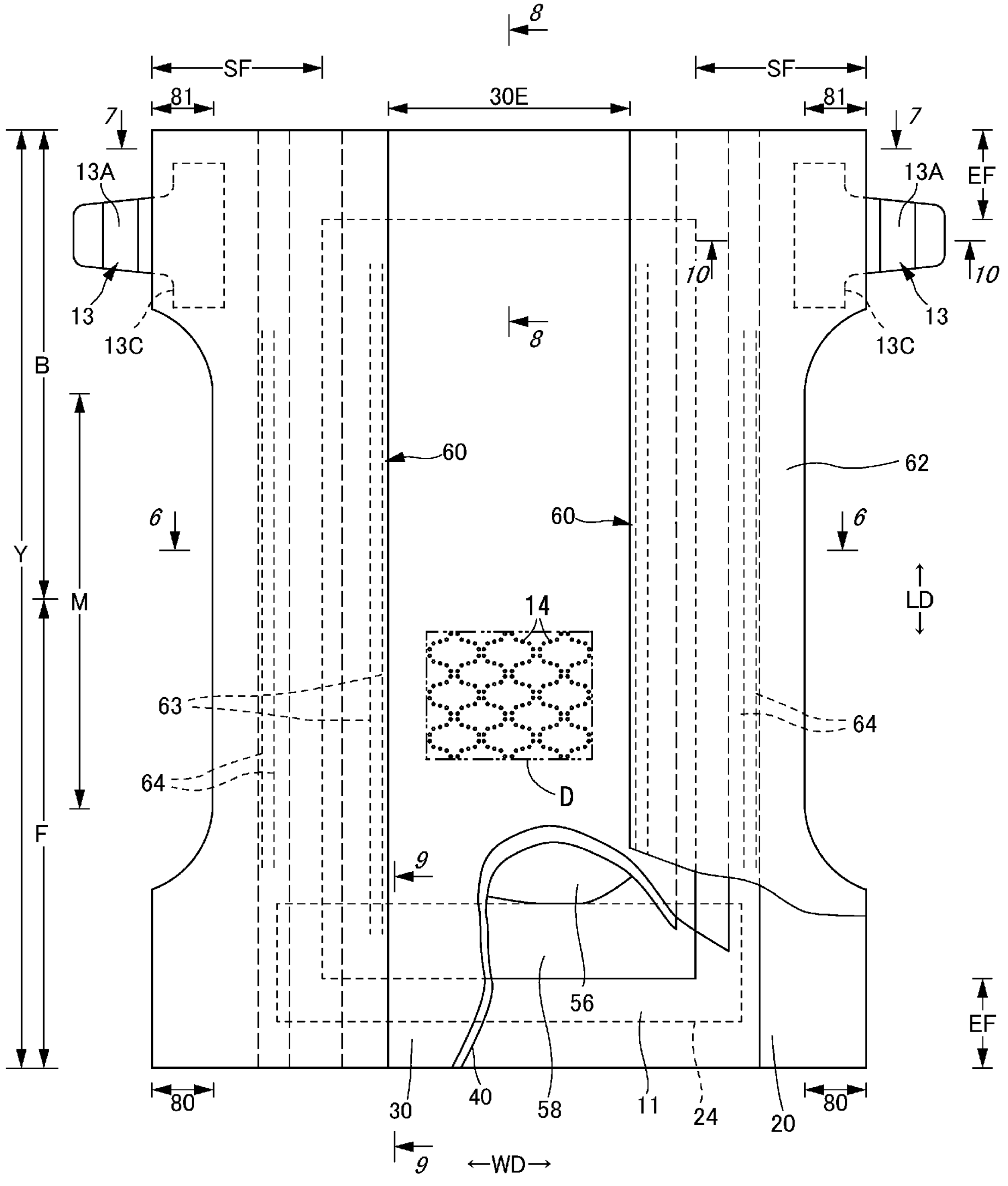

[FIG.2]
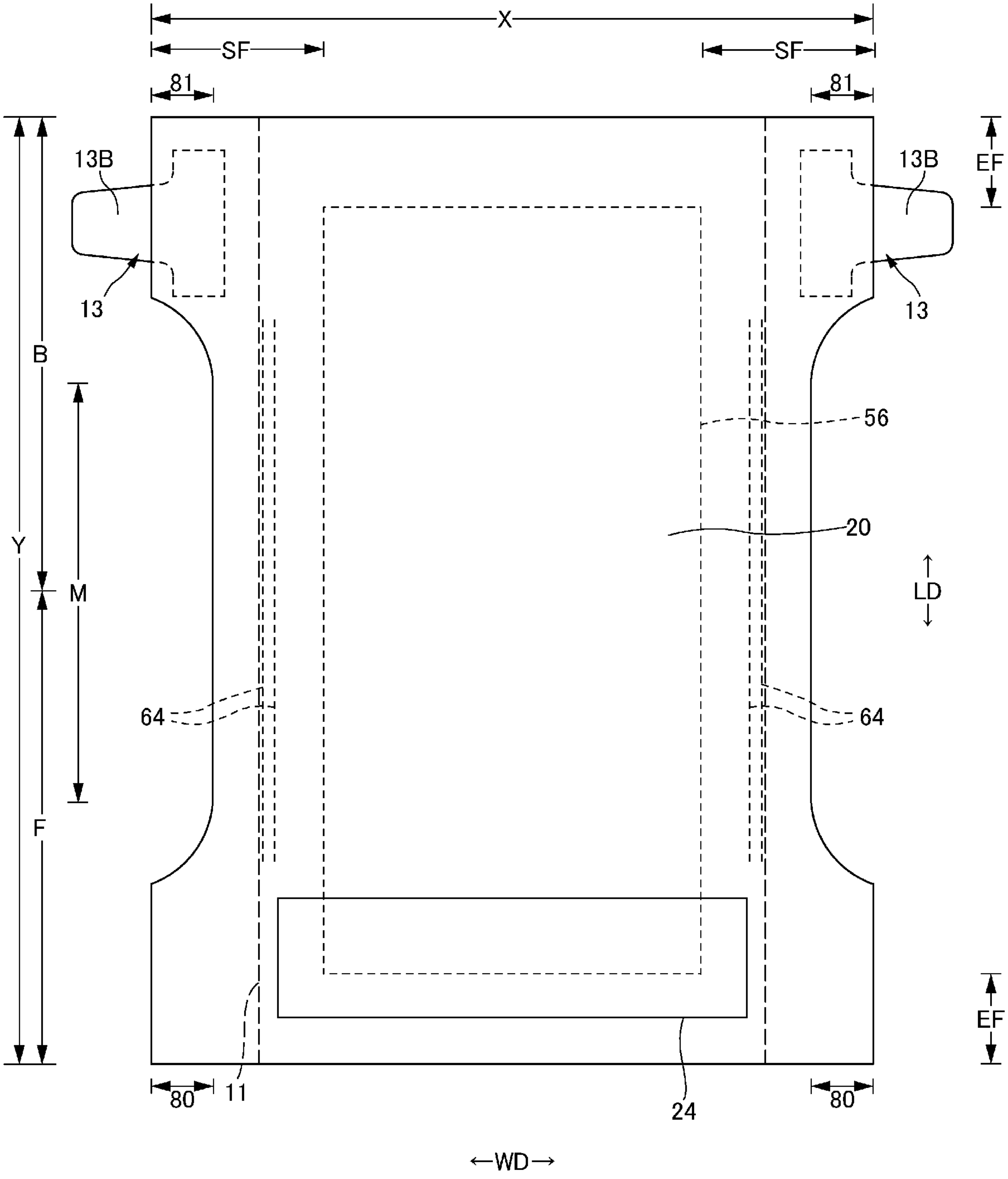

【FIG.3】
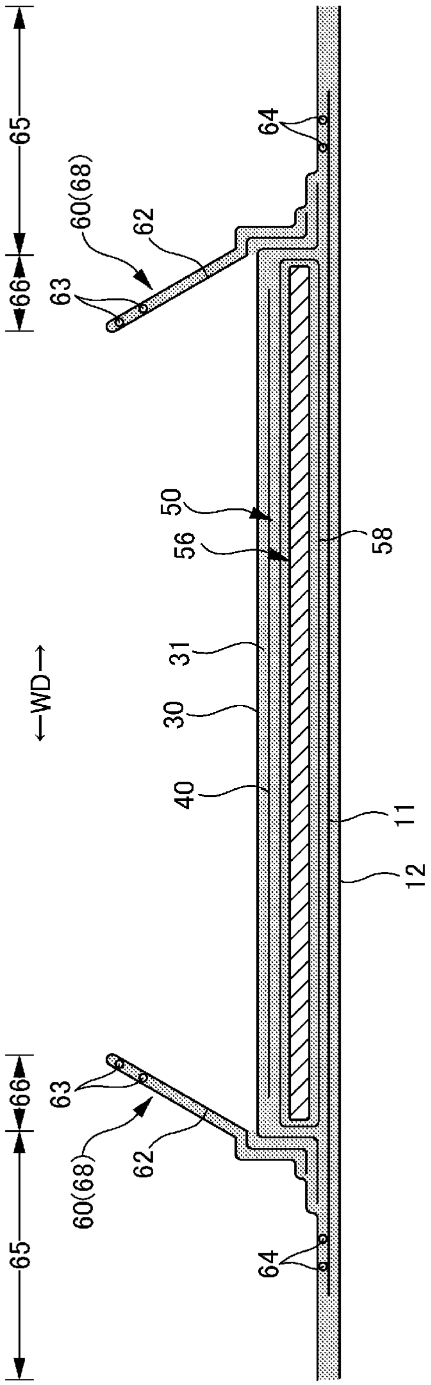

【FIG.4】
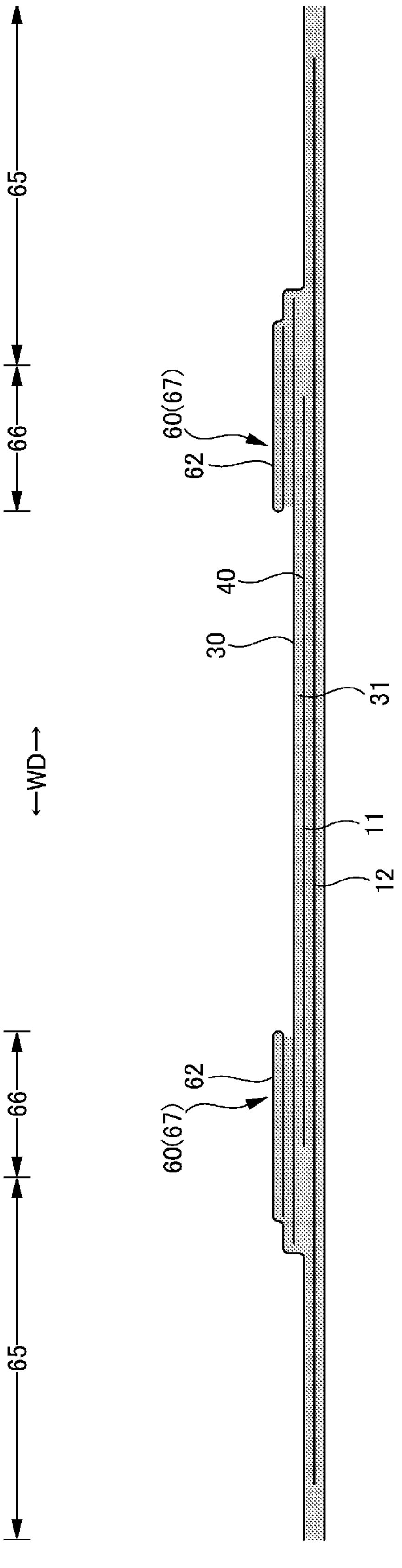

[FIG.5]
(a)
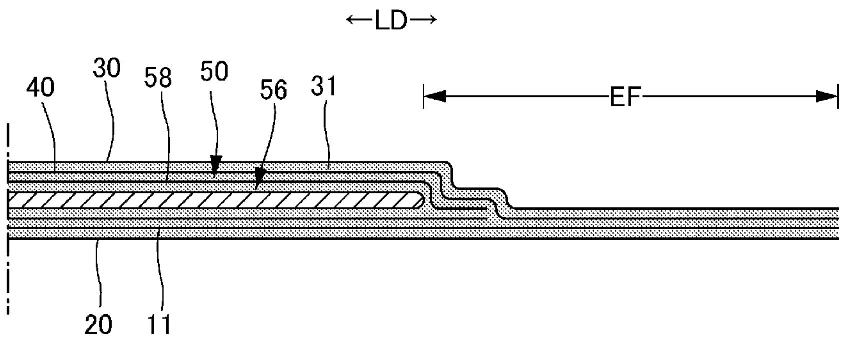
(b)
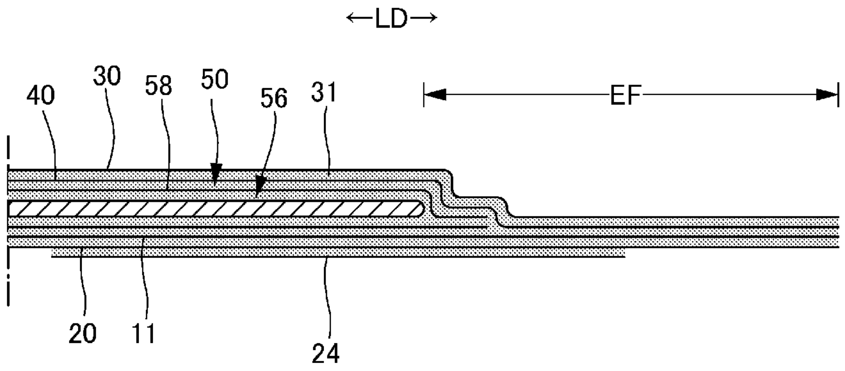
(c)
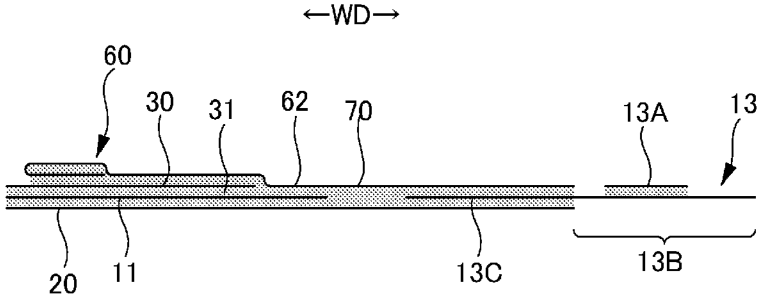

【FIG.6】
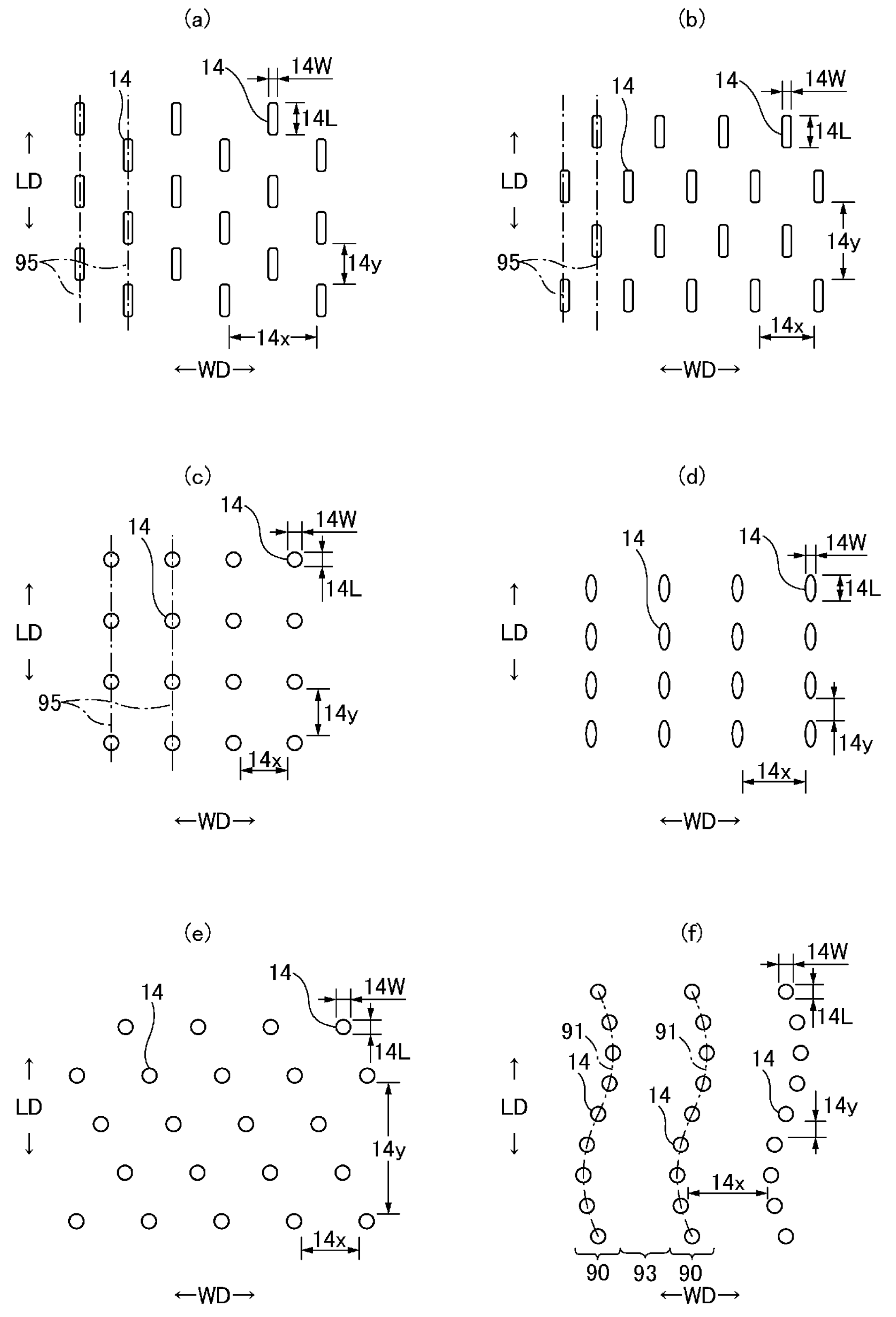

[FIG.7]
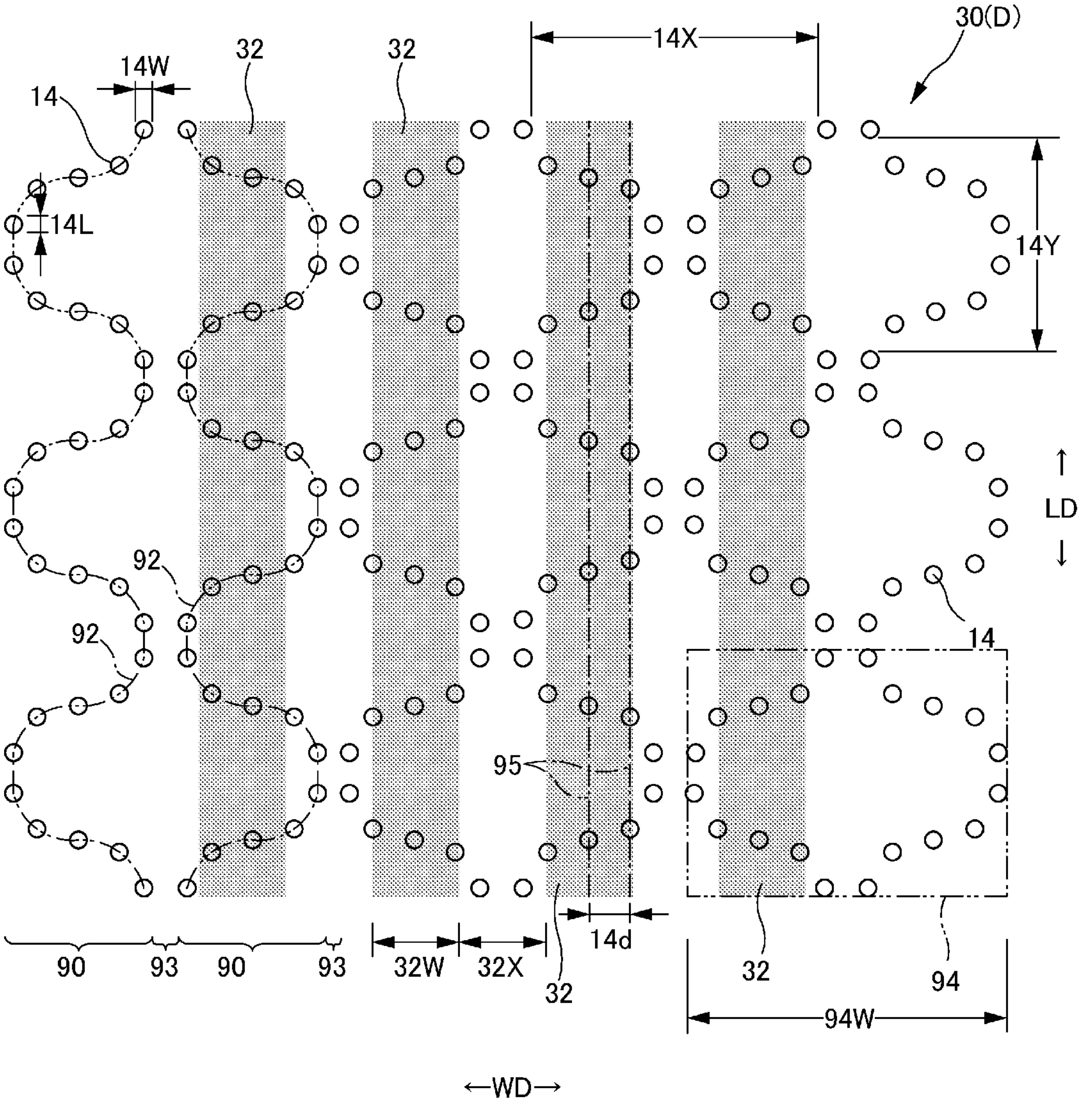

[FIG.8]
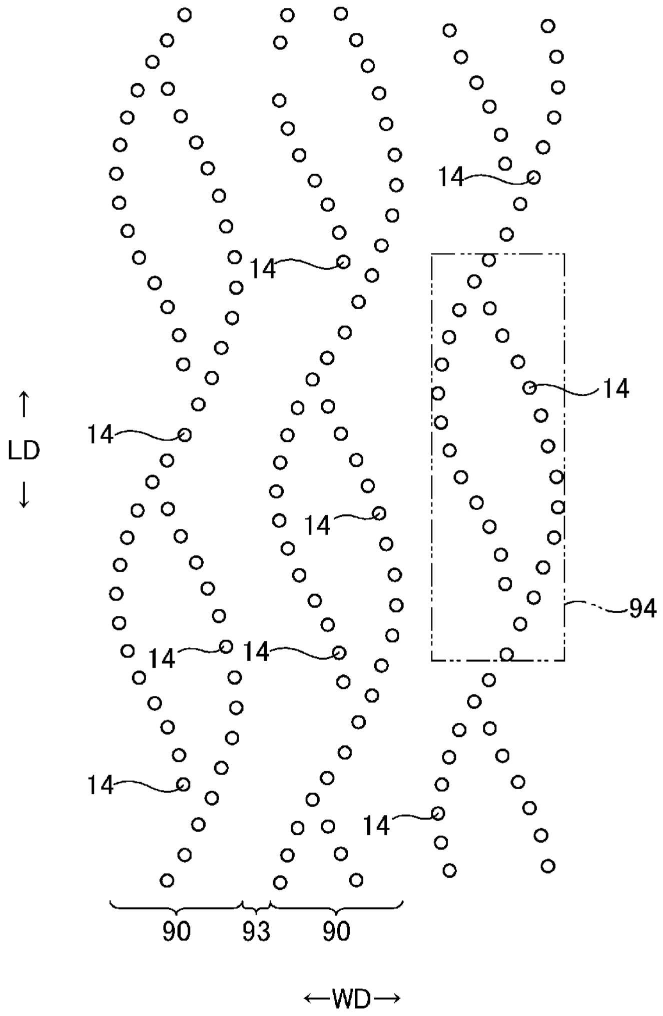

[FIG.9]
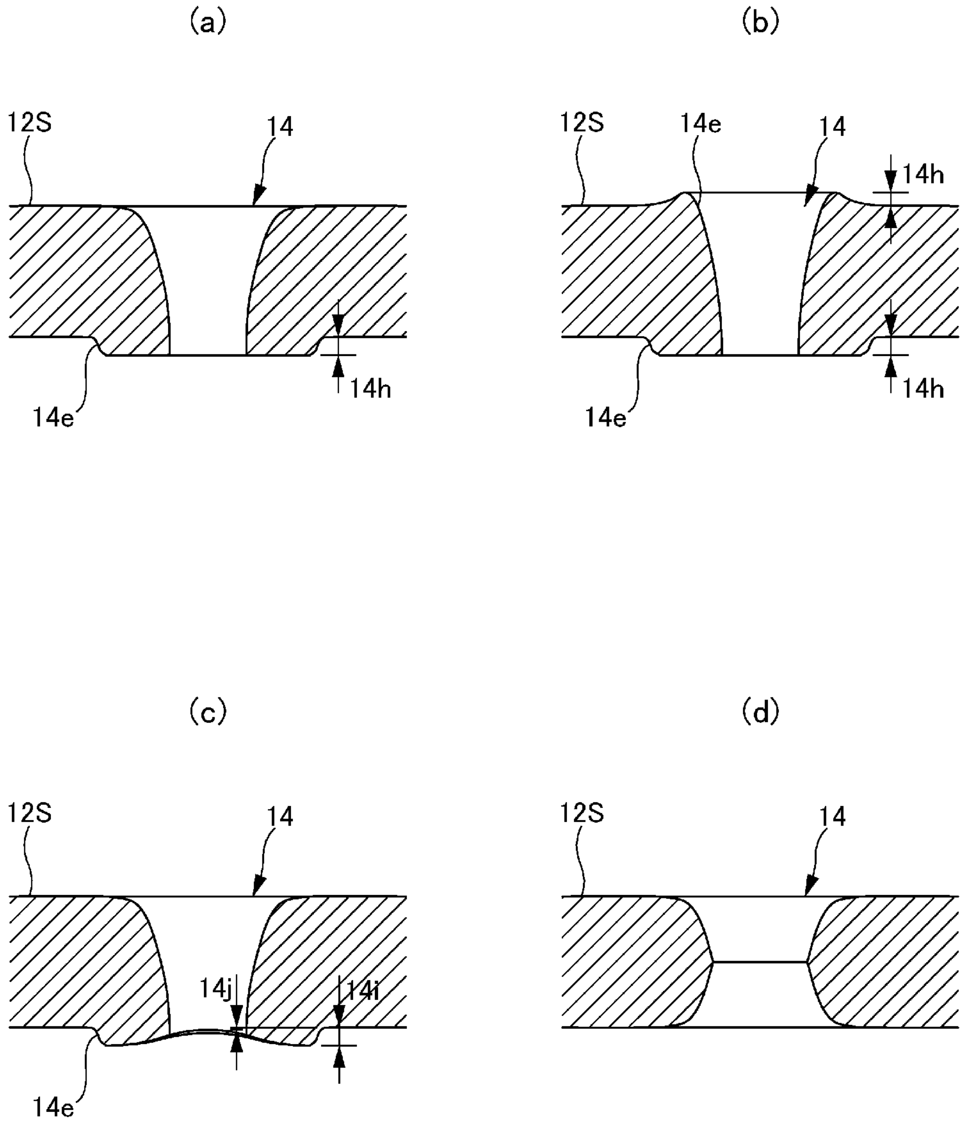

[FIG.10]
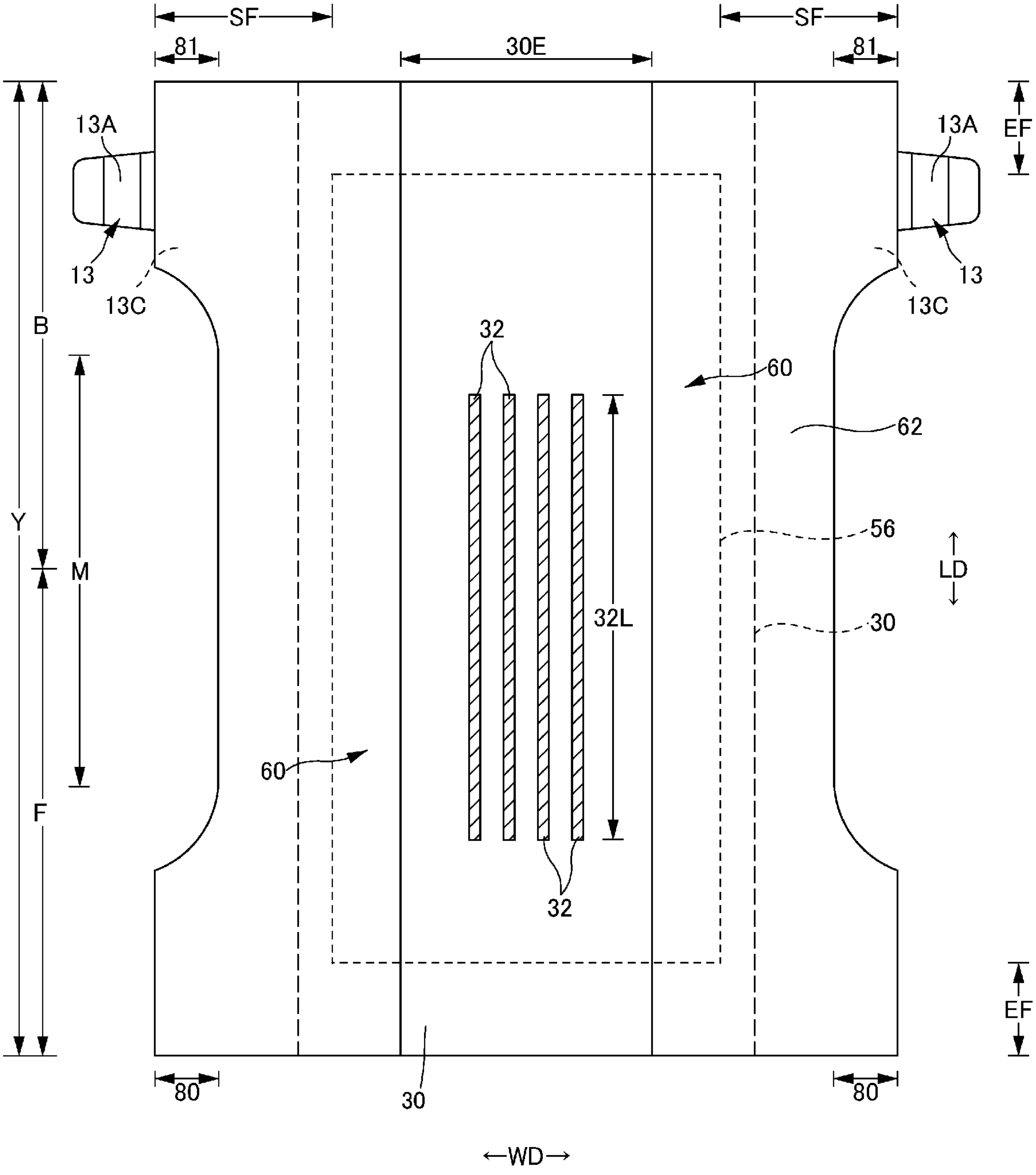

[FIG.11]
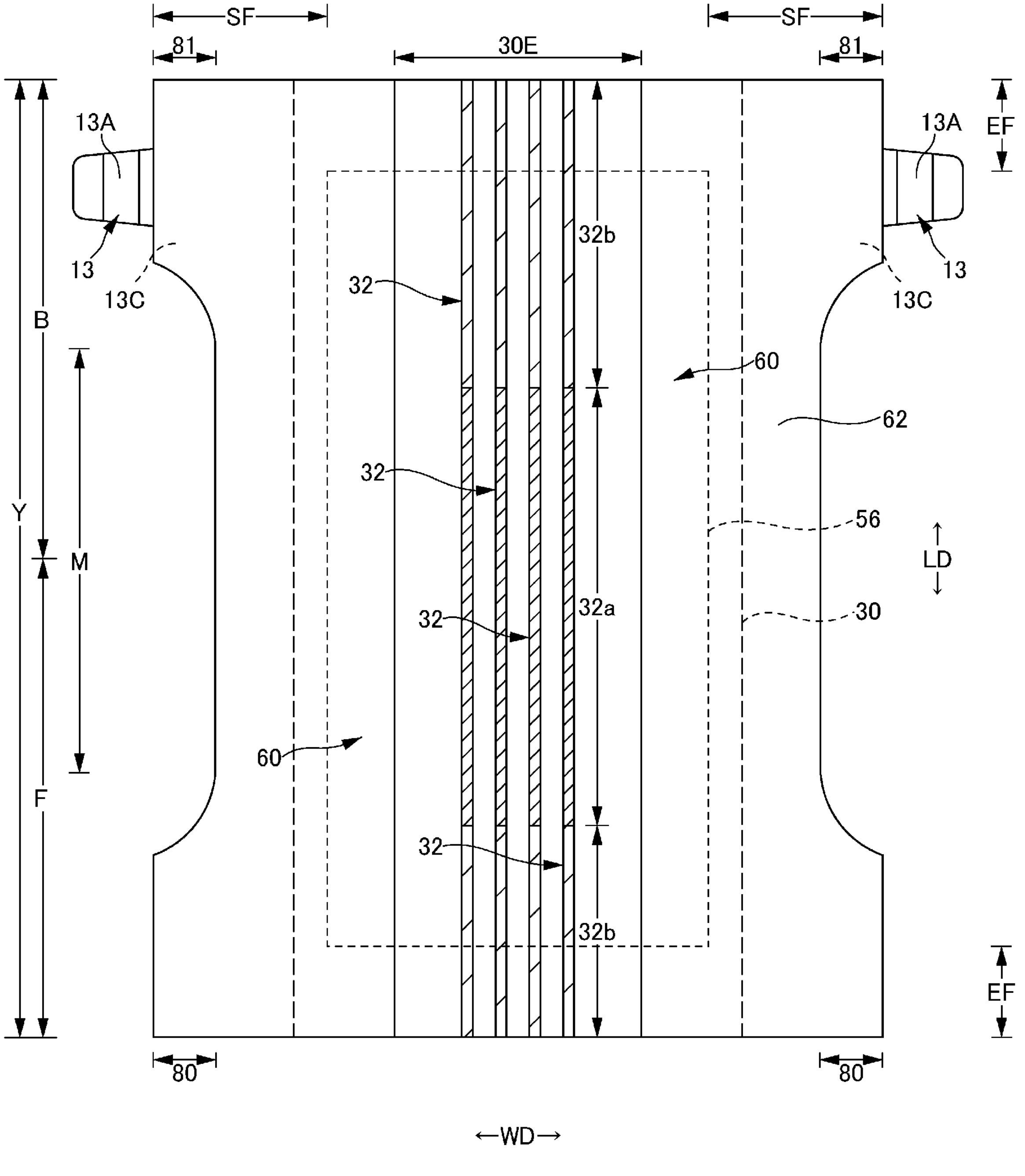

【FIG.12】
(a)
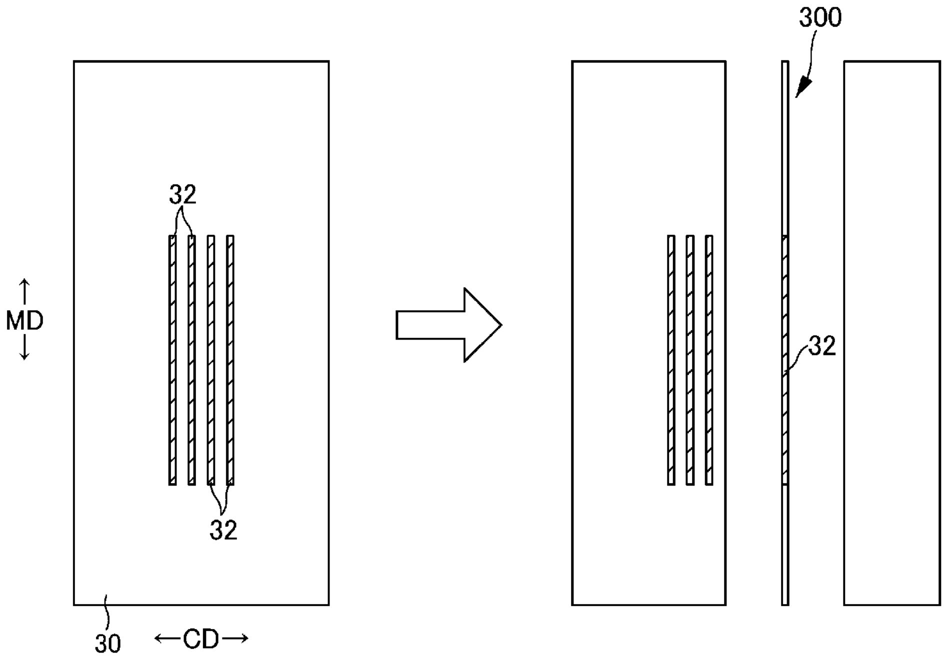
(b)
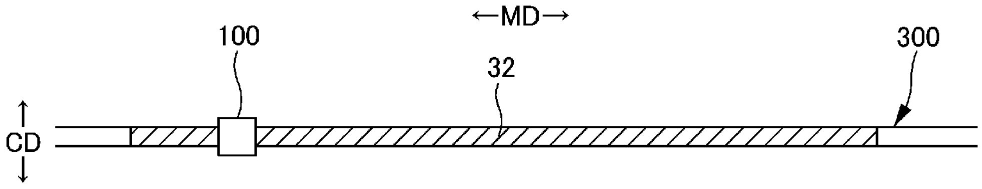

[FIG.13]
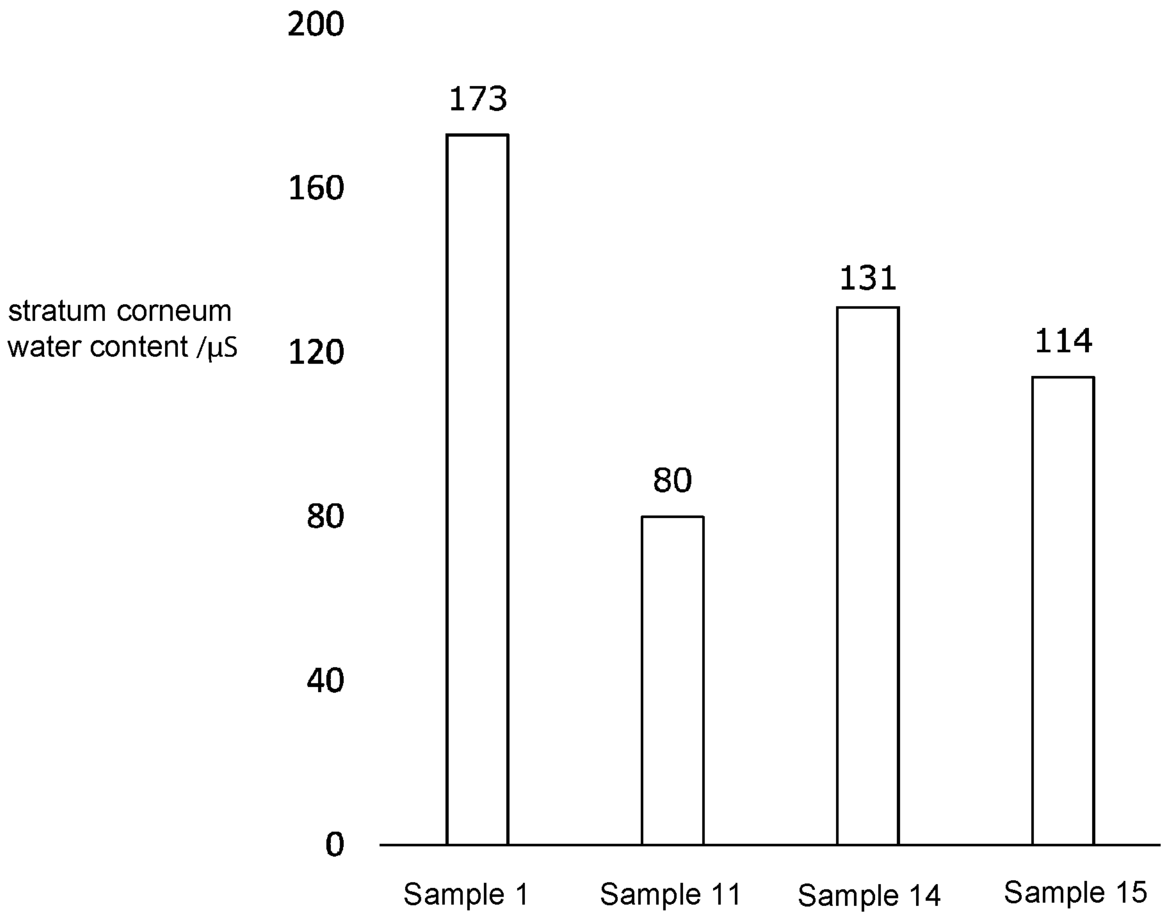

[FIG.14]
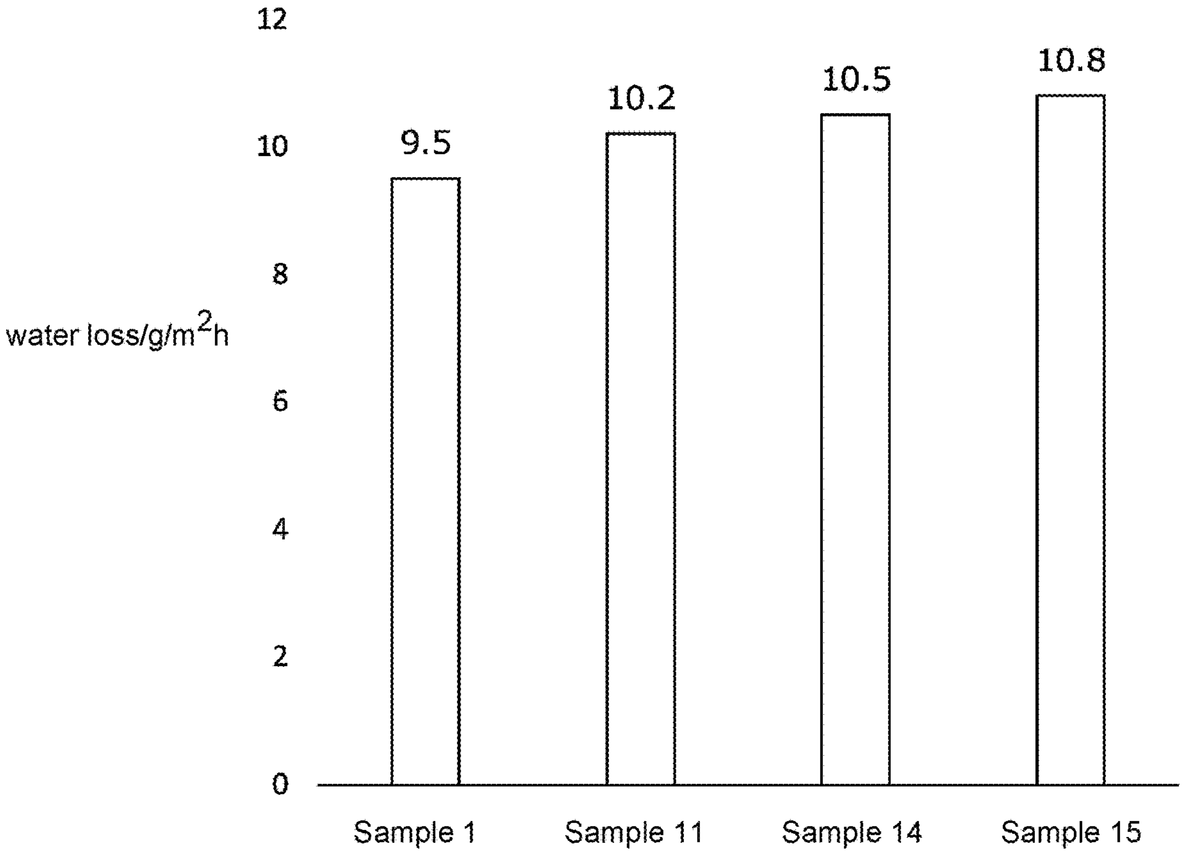

[FIG.15]
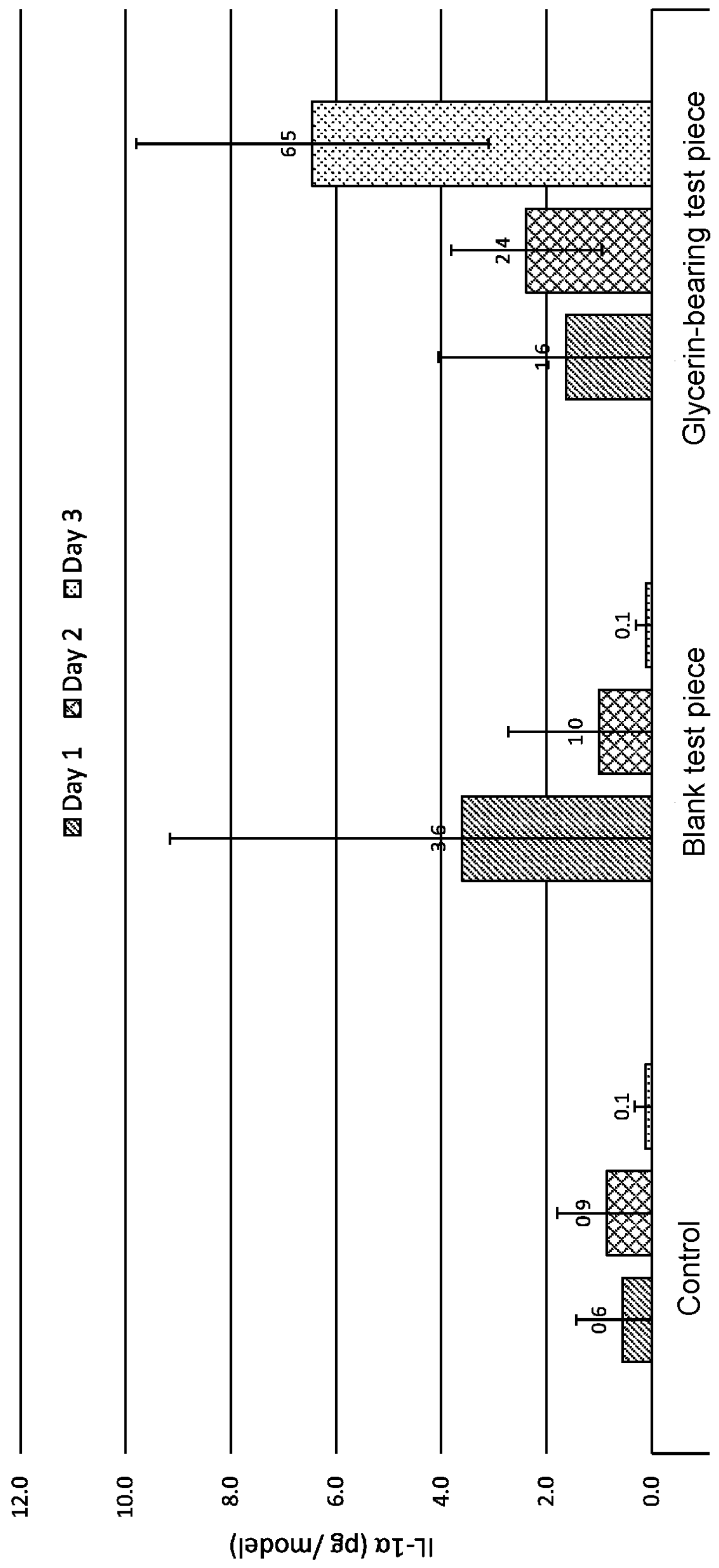

[FIG.16]
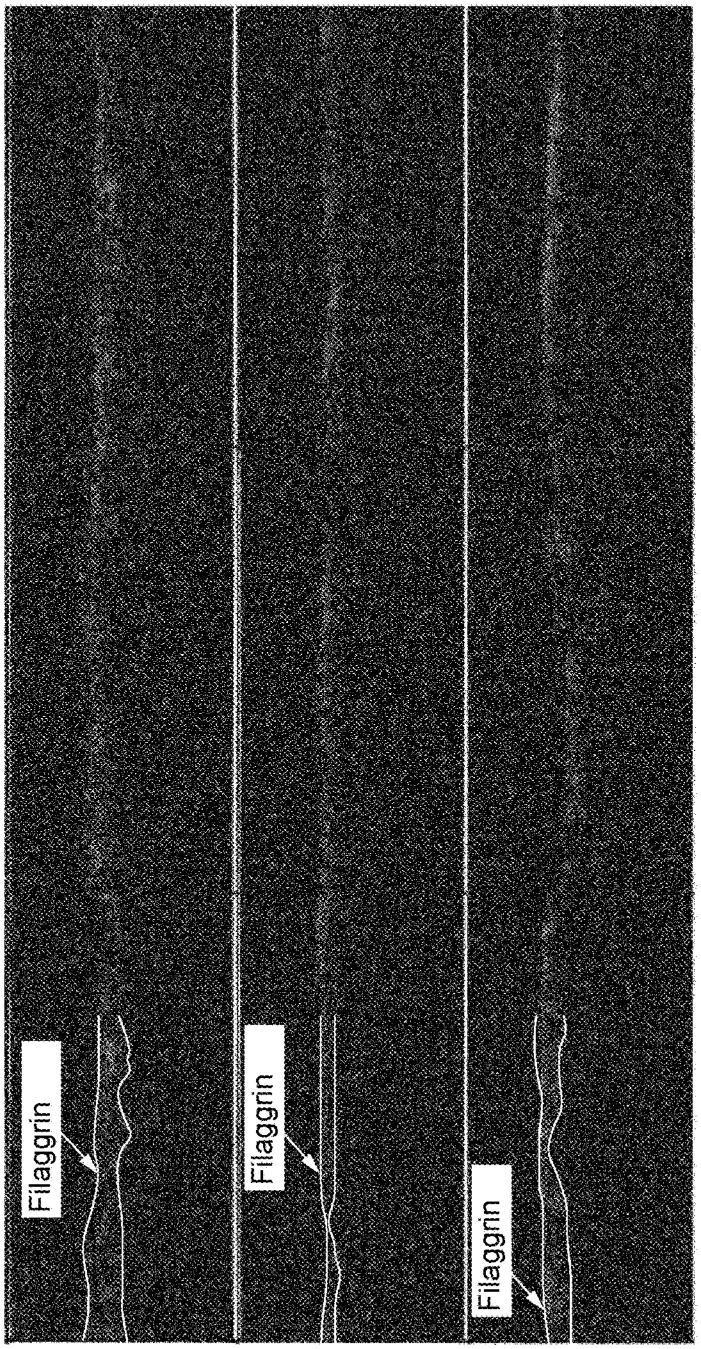
Control
Blank test piece
Glycerin-bearing test piece

DISPOSABLE WEARABLE ARTICLE

CROSS-REFERENCE TO RELATED APPLICATIONS

This application is the U.S. national stage application of International Application PCT/JP2020/019189, filed May 20, 2021, which international application was published on Dec. 2, 2021, as International Publication WO 2021/241396 in the Japanese language. The International Application claims priority of Japanese Patent Application No. 2020-094371, filed May 29, 2020. The international application and Japanese application are both incorporated herein by reference, in entirety.

TECHNICAL FIELD

The present invention relates to disposable wearable articles, including disposable diapers and sanitary napkins.

BACKGROUND ART

Disposable wearable articles, in particular, disposable diapers, often pose skin problems, particularly, skin rash of wearers. Such problems may result from physical irritation (friction or coarseness) to the skin or decrease in a barrier function of cutis caused by skin dryness of wearers.

There is proposed to cause a wax-like substance having a higher softening point than the human body temperature to be contained in a nonwoven top sheet for reducing friction between the skin of a wearer and the top sheet (Patent Literature 1).

For the purpose of reducing friction and the like, there is also known to apply a hydrophilic lotion to a nonwoven top sheet (Patent Literature 2). This hydrophilic lotion is preferred for its capability of avoiding hardness of the wax-like substance or lowering of liquid-permeability. In particular, a water-containing hydrophilic lotion is preferred for keeping the skin from drying.

However, there is still room for improvement as for suppression of diaper rash. For example, since infants have sensitive skin, the so-called diaper rash is likely to be occurred on their skin.

CITATION LIST

Patent Literature

Patent Literature 1: JP H08-52175 A

Patent Literature 2: JP 2010-526630 A

Patent Literature 3: JP 2002-509457 A

Patent Literature 4: JP 2019-170534 A

SUMMARY OF INVENTION

Technical Problem

It is therefore a primary object of the present invention to provide disposable wearable articles having a beneficial effect on the prevention of skin rash.

Solution to Problem

A disposable wearable article that has solved the above problem is as follows.

<First Aspect>

A disposable wearable article including a top sheet having a skin-touching region that is brought into contact with skin of a wearer, wherein the top sheet is made from nonwoven fabric having a fineness of 1 to 3 dtex, and a basis weight of 10 to 30 g/m$^2$, and wherein the skin-touching region has a glycerin-bearing zone bearing 0.7 to 2.7 g/m$^2$ of glycerin.

Effect

The present disposable wearable article is characterized in that in the top sheet bearing glycerin and being made from the nonwoven fabric, the prescribed content of glycerin per unit area is combined with the nonwoven fabric formed of fine fibers to be employed for the top sheet. In such a top sheet, the fine fibers contribute to reduce friction on a front face of the top sheet, which, in cooperation with the friction-reducing effect of glycerin, improves the overall friction-reducing effect. In addition, retainability of glycerin is improved by the fine fibers, to thereby further improve the friction-reducing effect. Moreover, glycerin moves from the top sheet to cutis of the wearer (and in particular, penetrates through stratum corneum) so as to moisturize the cutis of the wearer (and prevent the skin dryness). Therefore, in the present disposable wearable article, a function to reduce physical irritation to the cutis of the wearer and a function to moisturize the cutis of the wearer coexist to a high degree. As a result, the present disposable wearable article has a particularly beneficial effect on the prevention of skin rash.

Note that "skin-touching region" refers to a region which is exposed on a top face of the article in its spread state.

<Second Aspect>

The disposable wearable article according to the first aspect, wherein the glycerin-bearing zone has a MD (Machine Direction) dimension of 5 mm or more and a CD (Cross Direction) dimension of 5 mm or more, and wherein an area ratio of the glycerin-bearing zone to the skin-touching region is 3% or more.

Effect

The dimensions and the area ratio of the glycerin-bearing zone within the above ranges in the present aspect make the top sheet excellent in the function to reduce physical irritation to the cutis of the wearer and the function to moisturize the cutis of the wearer.

<Third Aspect>

The disposable wearable article according to the first or second aspect, wherein an amount of IL-1α secretion measured by bringing the glycerin-bearing zone of the top sheet into contact with a three-dimensional cultured skin model is one-half or less of that measured in a case of another sheet being different from the top sheet only in that the other sheet does not bear glycerin.

Effect

IL-1α (Interleukin-la) is proinflammatory cytokine produced in cutis which receives irritation causing skin rash (erythema). That is, the amount of IL-1α secretion measured by bringing the glycerin-bearing zone of the top sheet into contact with the three-dimensional cultured skin model is small as in the present aspect, which enables the top sheet to have an excellent ability to prevent the skin rash. Note that a method for measuring the amount of IL-1α secretion is to be discussed later.

<Fourth Aspect>

The disposable wearable article according to any one of the first to third aspects, wherein an amount of filaggrin measured by bringing the glycerin-bearing zone of the top sheet into contact with a three-dimensional cultured skin model is larger than that measured in a case of another sheet being different from the top sheet only in that the other sheet does not bear the glycerin.

Effect

Filaggrin is one of main ingredients of the stratum corneum and is largely concerned with strength and flexibility of the stratum corneum. It is known that if the amount of filaggrin is insufficient, corneocytes are peeled off easily and further, transepidermal water loss (TEWL) is increased. In addition, since filaggrin is degraded to be a natural moisturizing factor (NMF), it has also a function to moisturize the stratum corneum and a function to keep pH level thereof. That is, the amount of filaggrin secretion measured by bringing the glycerin-bearing zone into contact with the three-dimensional cultured skin model is large as in the present aspect, which enables the top sheet to have an excellent ability to prevent the skin rash. Note that a method for measuring the amount of filaggrin is to be discussed later.

<Fifth Aspect>

The disposable wearable article according to any one of first to fourth aspects, wherein the nonwoven fabric is nonwoven fabric formed of hydrophilized fibers in which hydrophobic resin fibers have been coated with a hydrophilizer.

Effect

The nonwoven fabric for the top sheet is preferably formed of hydrophobic resin fibers for their low cost, which as they are have poor retainability of glycerin. Accordingly, in the present aspect, it is preferred to use the nonwoven fabric formed of hydrophilized fibers with a hydrophilizer to improve the glycerin-retainability of the fiber nonwoven fabric.

Advantageous Effects of Invention

The present invention provides advantages such as a beneficial effect on the prevention of skin rash.

BRIEF DESCRIPTION OF DRAWINGS

FIG. 1 is a plan view of a tape-type disposable diaper in its spread state, illustrating the interior surface thereof.

FIG. 2 is the plan view of the tape-type disposable diaper in its spread state, illustrating the exterior surface thereof.

FIG. 3 is a cross-sectional view taken along line 6-6 in FIG. 1.

FIG. 4 is a cross-sectional view taken along line 7-7 in FIG. 1.

FIG. 5(*a*) is a sectional view taken along line 8-8 in FIG. 1, FIG. 5(*b*) is a sectional view taken along line 9-9 in FIG. 1, and FIG. 5(*c*) is a sectional view taken along line 10-10 in FIG. 1.

FIG. 6 shows plan views of various examples of the aperture pattern in the perforated nonwoven fabric.

FIG. 7 is a plan view illustrating an example of the aperture pattern (Moroccan pattern) in the perforated nonwoven fabric.

FIG. 8 is a plan view illustrating an example of the aperture pattern (chain pattern) in the perforated nonwoven fabric.

FIG. 9 shows sectional views of the apertures in the perforated nonwoven fabric.

FIG. 10 is a plan view of a tape-type disposable diaper in its spread state, illustrating the interior surface thereof.

FIG. 11 is a plan view of a tape-type disposable diaper in its spread state, illustrating the interior surface thereof.

FIG. 12 shows plan views for explaining a specimen.

FIG. 13 is a graph showing measurement results of stratum corneum water content.

FIG. 14 is a graph showing measurement results of transepidermal water loss (TEWL).

FIG. 15 is a graph showing measurement results of amount of IL-1α secretion.

FIG. 16 is a photograph showing observation results of amount of filaggrin.

DESCRIPTION OF EMBODIMENTS

FIGS. 1 to 5 show a tape-type disposable diaper as an example of a disposable wearable article. In the figures, reference sign X refers to the overall width of the diaper exclusive of the connecting tapes, whereas reference sign Y refers to the overall length of the diaper. In the sectional views, dotted pattern regions represent an adhesive as joining means for joining various components. A hot melt adhesive may be applied using a known technique, such as slot application, bead application in continuous lines or dotted lines, spray application in spiral, Z, or wave shapes, or pattern coating (transfer of a hot melt adhesive by relief printing). In place of or in addition to these, fixing portions of elastic members may be fixed to adjacent members by application of a hot melt adhesive to the outer peripheral surface of the elastic members. Examples of the hot melt adhesive include, but not limited to, EVA-based, pressure-sensitive rubber-based (elastomer-based), polyolefin-based, and polyester/polyamide-based adhesives. The joining means for joining various components may alternatively be material melt-bonding, such as heat sealing or ultrasonic sealing.

As the nonwoven fabric in the description hereinbelow, commonly known nonwoven fabric may suitably be used depending on the parts or purposes. Examples of the constituent fibers of the nonwoven fabric include, but not limited to, synthetic fibers, such as polyolefin-based, e.g., polyethylene or polypropylene, polyester-based, or polyamide-based fibers (including not only single component fibers, but also composite fibers, such as of core/sheath type), as well as regenerated fibers, such as rayon or cupra, or natural fibers, such as cotton, and also mixtures thereof. For improved flexibility of the nonwoven fabric, the constituent fibers may preferably be crimped fibers. The constituent fibers of the nonwoven fabric may also be hydrophilic fibers (including those rendered hydrophilic with hydrophilizers), hydrophobic fibers, or water-repelling fibers (including those rendered water-repelling with water repellents). Further, nonwoven fabric may generally be categorized into discontinuous fiber nonwoven fabric, continuous fiber nonwoven fabric, spunbonded nonwoven fabric, melt blown nonwoven fabric, spunlace nonwoven fabric, thermal bonded (air through) nonwoven fabric, needle-punched nonwoven fabric, point-bonded nonwoven fabric, composite nonwoven fabric (SSS nonwoven fabric having the same or similar nonwoven layers laid one on top of another, as well as SMS or SMMS nonwoven fabric having different nonwoven layers laid one on top of another, i.e., melt blown layer interposed between spunbonded layers), or the like, generally depending on the length of the fibers, method of forming the sheet, method of joining the fibers, or layered structure, and any of these nonwoven fabric may be used. The composite nonwoven fabric refers to those having all the layers integrally manufactured and subjected to fiber joining process all over the layers, and does not include those having a plurality of nonwoven fabric layers separately manufactured and bonded with joining means, such as hot melt adhesives.

The present tape-type disposable diaper has a ventral section F extending forward of the middle of the diaper in the front-back direction LD and a dorsal section B extending backward of the middle of the diaper in the front-back direction LD. The present tape-type disposable diaper is configured with a crotch section M extending from forward of the middle of the product to backward of the middle of the product in the front-back direction, front wings 80 extending on opposed sides in the right-left direction at a position spaced forward of the middle of the product in the front-back direction, and back wings 81 extending on opposed sides in the right-left direction at a position spaced backward of the middle of the product in the front-back direction. Further, the present tape-type disposable diaper includes an absorber body 56 internally disposed within a region including the crotch section, a liquid-pervious top sheet 30 covering the top side of the absorber body 56, a liquid-impervious sheet 11 covering the underside of the absorber body 56, and an exterior nonwoven sheet 12 covering the underside of the liquid-impervious sheet 11 to constitute the product exterior surface.

Materials and features of each part will now be explained in turn.

(Absorber Body)

The absorber body 56 absorbs and holds excreted fluid, and may be formed of an assembly of fibers. Such an assembly of fibers may be a stack of discontinuous fibers of fluff pulp, synthetic fibers, or the like, as well as an assembly of filaments obtained by opening, where necessary, tows (fiber bundles) of synthetic fibers, such as cellulose acetate. The basis weight of the fibers may be about 100 to 300 g/m$^2$ for a stack of fluff pulp or discontinuous fibers, and about 30 to 120 g/m$^2$ for an assembly of filaments. The fineness of the synthetic fibers, when used, is, for example, 1 to 16 dtex, preferably 1 to 10 dtex, more preferably 1 to 5 dtex.

The plan shape of the absorber body 56 may suitably be decided, and may be in a rectangular shape or a shape having a middle portion in the front-back direction LD narrowed so as to fit around each leg.

(Superabsorbent Polymer Particles)

The absorber body 56 may be caused partially or entirely to contain superabsorbent polymer particles. The superabsorbent polymer particles include not only “particles”, but also “powders”. Superabsorbent polymer particles used in this type of absorbent articles may be used as they are as the superabsorbent polymer particles here. The particle size of the superabsorbent polymer particles is not particularly limited and, for example, the particles may preferably have such a particle size that, when the particles are subjected to sieving (five-minute shaking) through a 500 μm standard sieve (JIS Z8801-1: 2006), followed by further sieving (five-minute shaking) through a 180 μm standard sieve (JIS Z8801-1: 2006) of the particles sieved through the previous sieve, the percentage of the particles remaining on the 500 μm standard sieve is 30 wt % or less and the percentage of the particles remaining on the 180 μm standard sieve is 60 wt % or more.

Any materials of the superabsorbent polymer particles may be used without particular limitation, and those having a water absorption of 40 g/g or more are preferred. The superabsorbent polymer particles may be starch-based, cellulose-based, or synthetic polymer-based, and starch-acrylic acid (salt) graft copolymers, saponified products of starch-acrylonitrile copolymers, cross-linked sodium carboxymethyl cellulose, or acrylic acid (salt) polymers may be used. The superabsorbent polymer particles may preferably be in ordinary powder or granular form, but particles in other forms may also be used.

The superabsorbent polymer particles having a water absorption rate of 70 seconds or less, particularly 40 seconds or less, may preferably be used. With too slow a water absorption rate, the absorber body 56 is likely to undergo so-called returning, wherein liquid supplied into the absorber body 56 returns out of the absorber body 56.

The superabsorbent polymer particles may preferably be those having a gel strength of 1000 Pa or higher. With such property, when the superabsorbent polymer particles are formed into a bulky absorber body 56, stickiness after liquid absorption may effectively be limited.

The basis weight of the superabsorbent polymer particles may suitably be decided depending on the absorption amount required in a use of the absorber body 56. Thus, it depends, but the basis weight may usually be 50 to 350 g/m$^2$.

(Wrapping Sheet)

For limiting escape of the superabsorbent polymer particles, or for improving maintenance of the shape of the absorber body 56, the absorber body 56 may be wrapped with a wrapping sheet 58 to produce an absorbent element 50, which is to be disposed inside. The wrapping sheet 58 may be tissues, in particular, crepe paper, nonwoven fabric, polyethylene-laminated nonwoven fabric, perforated sheet, or the like, provided that sheets through which the superabsorbent polymer particles will not escape are preferred. When nonwoven fabric is used in place of crepe paper, hydrophilic SMMS (spunbonded/melt-blown/melt-blown/spunbonded) nonwoven fabric is particularly preferred, which may be made of polypropylene, polyethylene/polypropylene, or the like. The basis weight is preferably 5 to 40 g/m$^2$, particularly 10 to 30 g/m$^2$.

One such wrapping sheet 58 may be used, as shown in FIG. 3, to wrap the entire absorber body 56, or a plurality of sheets, such as an upper sheet and a lower sheet, may be used to wrap the entire absorber body 56. Alternatively, the wrapping sheet 58 may be omitted.

(Top Sheet)

The top sheet 30 extends in the front-back direction from the front end to the back end of the product, and in the width direction WD laterally beyond the absorber body 56, but its shape may suitably be modified, for example, so that the width of the top sheet 30 is shorter than the entire width of the absorber body 56, in case, for example, the starting points of standup gather parts 60 to be discussed later are located on the center side of the side edges of the absorber body 56 in the width direction WD, or otherwise required.

The top sheet 30 has a skin-touching region 30E that is brought into contact with skin of a wearer, and is preferably made from nonwoven fabric in light of liquid permeability and texture. Various nonwoven fabric may be used as the top sheet 30 but, in view of cushioning property, flexibility, permeability of loose stool (watery or muddy stool), or the like factors, discontinuous fiber nonwoven fabric, such as air-through nonwoven fabric, is preferred rather than continuous fiber (long fiber) nonwoven fabric and, usually, discontinuous fiber nonwoven fabric generally having a fineness of 1 to 10 dtex, a basis weight of 10 to 30 g/m$^2$, and a thickness of 0.4 to 1.4 mm, is preferred. The fiber length of the discontinuous fiber nonwoven fabric is not particularly limited, and is preferably about 0.5 to 1.0 mm.

The top sheet 30 is particularly preferably is perforated nonwoven fabric having an aperture arrayed region wherein apertures 14 each penetrating two sides of the fabric are arrayed in a particular pattern. The shape and size of each aperture 14, the pattern of the array, or the like, may suitably be decided. Note that, in FIG. 1, for ready conception of the figure, the apertures 14 are illustrated only in a part D of the top sheet 30, which, however, does not represent the aperture arrayed region.

The aperture arrayed region may be positioned only in the middle of the top sheet 30 in the front-back direction LD or only in the middle of the top sheet 30 in the width direction WD (the top sheet 30 may partially have a zone without any aperture 14). Alternatively, the aperture arrayed region may be provided all over the top sheet 30. That is, the aperture arrayed region may extend, as long as it is provided over the skin-touching region 30E, to the other region (for example, the regions where the gathered sheets 62 are bonded on opposed sides in the width direction WD).

The plan shape of each aperture 14 (opening shape) may suitably be decided. Each aperture 14 may be in a slot shape as shown in FIGS. 6(*a*) and 6(*b*), perfect circular as shown in FIGS. 6(*c*), 6(*e*), and 6(*f*) as well as in FIGS. 7 and 8, elliptical as shown in FIG. 6(*d*), polygonal, such as triangular, rectangular, or rhombic, start shaped, cloud shaped, or any arbitrary shape. Though not shown, apertures 14 of different shapes may be present. The size of each aperture 14 is not particularly limited, and the dimension 14L in the front-back direction (the maximum dimension) is preferably 0.5 to 2.0 mm, particularly 0.5 to 1.0 mm, and the dimension 14W in the width direction (the maximum dimension) is preferably 0.5 to 2.0 mm, particularly 0.5 to 1.0 mm. When the shape of each aperture 14 is longer in the front-back direction (the maximum dimension in one direction is longer than the overall dimension in the direction orthogonal thereto), such as a slot, elliptical, rectangular, or rhombic shape, the front-back dimension is preferably 1.2 to 2.5 times the dimension in the width direction orthogonal thereto.

Further, when the shape of each aperture 14 is longer in one direction, the longitudinal direction of the apertures 14 is preferably aligned to the machine direction (MD) of the nonwoven fabric, but may be aligned to the cross direction (CD) or oblique thereto. Note that the MD of the perforated nonwoven fabric constituting the top sheet 30 is, in most cases, aligned to the front-back direction LD.

The area of each aperture 14 and the area ratio of the apertures in the aperture arrayed region may suitably be decided, and the area may preferably be about 0.25 to 4.00 mm$^2$ and the area ratio may preferably be about 0.1 to 10%.

The pattern of the array of the apertures 14 may suitably be decided. For example, as shown in FIGS. 6(*a*), 6(*c*), and 6(*d*), it is preferred that the pattern of the array of the apertures 14 is a matrix wherein lines of apertures 14 aligned linearly in the front-back direction LD at predetermined intervals are repeated in the width direction WD at predetermined intervals. In this case, the apertures 14 may be arranged with the intervals 14$y$ of the apertures 14 in the front-back direction LD being smaller than the intervals 14$x$ of the apertures 14 in the width direction WD as shown in FIGS. 6(*a*) and 6(*d*), with the intervals 14$y$ of the apertures 14 in the front-back direction LD being generally equal to the intervals 14$x$ of the apertures 14 in the width direction WD as shown in FIG. 6(*c*), or with the intervals 14$y$ of the apertures 14 in the front-back direction LD being larger than the intervals 14$x$ of the apertures 14 in the width direction WD as shown in FIGS. 6(*b*) and 6(*e*). Further, as shown in FIGS. 6(*a*) and 6(*b*), the lines 95 of apertures aligned linearly in the front-back direction LD at predetermined intervals may be arranged in the width direction WD at intervals and shifted with each other in the front-back direction LD. FIGS. 6(*a*) and 6(*b*) show examples of the arrangement wherein the apertures 14 in the adjacent lines 95 are staggered, i.e., so-called staggered pattern (hexagonal lattice pattern).

The intervals 14$y$ of the apertures 14 in the front-back direction and the intervals 14$x$ of the apertures 14 in the width direction may respectively be constant or varied, which may suitably be decided. For example, the intervals 14$y$ of the apertures 14 in the front-back direction may be 0.9 to 8.0 mm, particularly 1.0 to 3.0 mm, whereas the intervals 14$x$ of the apertures 14 in the width direction may be 2.0 to 10 mm, particularly 3.0 to 5.0 mm.

The pattern of the array of apertures 14 may also be such that groups 90 of apertures 14 aligned in the front-back direction LD with each group forming a single wavy line 91, 92 are arranged in the width direction WD at intervals in the same or different phases as shown in FIGS. 6(*f*) and 7. In the example of the pattern as shown in FIG. 7, the wave phases of the groups 90 of apertures 14 adjacent to each other in the width direction WD are opposite, so that the imaginary lines connecting the apertures 14 form a Moroccan pattern (ogee pattern). In FIG. 7, reference sign 94 refers to a unit arrayed area whereas reference sign 94W refers to the dimension in the width direction WD of the unit arrangement portion. Further, as shown in FIG. 8, the pattern of the array of apertures 14 may also be such that groups 90 of apertures 14 aligned in the front-back direction LD at intervals with each group forming a chain-like pattern are arranged in the width direction WD at intervals. Here, "groups 90 of apertures 14 are arranged in the width direction WD at intervals" means that an imperforated zone 93 extending linearly unintermittently along the front-back direction LD is present between the groups 90 of apertures 14 adjacent to each other in the width direction WD.

The sectional shape of each aperture 14 is not particularly limited. For example, each aperture 14 may be a punched aperture of which periphery is formed with cut ends of fibers, or a non-punched aperture which hardly has cut ends of fibers on its periphery and is formed by inserting a pin into the space among fibers to expand (fiber density at the periphery is higher). The punched aperture may have a diameter tapered toward the middle of the thickness as shown in FIG. 9(*d*), or a diameter tapered toward one end in the thickness direction, not shown.

The non-punched aperture 14 has a diameter tapered from the pin-insertion side toward the opposite side of the aperture 14, which includes a diameter continuously tapered all over the thickness of a nonwoven fabric layer, and a diameter whose tapering is substantially ceased in the middle of the thickness. Such non-punched apertures include those as shown in FIGS. 9(*a*) and 9(*c*) wherein fibers at the periphery of each aperture 14 on the side opposite to the pin-insertion side are extruded from the side opposite to the pin-insertion side to form a protrusion (burr) 14*e*, whereas a protrusion 14*e* is not formed on the pin-insertion side, and those as shown in FIG. 9(*b*) wherein fibers at the periphery of each aperture 14 on the side opposite to the pin-insertion side are extruded to the side opposite to the pin-insertion side to form a protrusion 14*e*, whereas fibers at the periphery of the aperture on the pin-insertion side are extruded to the pin-insertion side to form a protrusion 14*e*. The apertures 14 of the former type further include those as shown in FIG. 9(*a*) wherein the height 14*h* of the protrusion 14*e* is substantially even, and those as shown in FIG. 9(*c*) wherein the height 14*i* of the protrusion 14*e* is highest at two opposed locations whereas the height 14*j* of the protrusion 14*e* is lowest at two opposed locations orthogonal to the highest locations. It is preferred that the protrusion 14*e* continuously extends along the circumferential direction of the aperture to form a cylinder, but it is also conceivable that protrusions 14*e* of part or all of the apertures 14 are formed partially along the circumferential direction of the respective apertures 14. The heights 14*h*, 14*i*, 14*j* of the protrusion (nominal height determined under optical microscope without pressure) are preferably about 0.2 to 1.2 mm. Further, it is preferred that the maximum height 14*i* of the protrusion 14*e* is about 1.1 to 1.4 times the minimum height 14*j* of the protrusion 14*e*. The height of protrusion 14*e* may vary along the circumferential direction of the aperture 14.

When an aperture 14 longer in one direction, for example, as shown in FIGS. 6(*a*), 6(*b*), 6(*d*), is formed by pin insertion, the fibers at the periphery of the aperture 14 are displaced outwards or vertically to form a protrusion (burr) 14*e* having a height 14*i* at the longitudinally opposed locations of the aperture 14 higher than a height 14*j* at the opposed locations orthogonal to the longitudinal. The protrusion 14*e* around the aperture 14 may have a fiber density lower than the density around the protrusion, but preferably have a fiber density similar to or higher than the density around the protrusion.

In particular, when the perforated nonwoven fabric is continuous fiber nonwoven fabric having a fineness of 0.1 to 5.0 dtex (more preferably 1.0 to 3.0 dtex), a basis weight of 15 to 20 g/m$^2$ (more preferably 15 to 18 g/m$^2$), and a thickness of 0.3 to 0.8 mm (more preferably 0.3 to 0.6 mm), and the apertures 14 are formed by pin insertion, the height of the protrusion 14*e* formed at the periphery of each aperture 14 is lower. More specifically, in the above-mentioned specific range of continuous fiber nonwoven fabric, the fibers are hard to be extruded in the thickness direction upon formation of the pin insertion apertures. This is because the fibers to which force is applied by the pin insertion are continuous and entangled all over the nonwoven fabric (continuous fiber), and displacement of a portion of the fibers to which force is applied by the pin insertion is withheld by the portions of the fibers continuous on the outer side thereof. Further, the above-mentioned specific range of continuous fiber nonwoven fabric basically has a moderately low fiber density, so that displacement of the fibers in the direction orthogonal to the thickness is relatively easy. As a result, when the above-mentioned specific range of continuous fiber nonwoven fabric is subjected to the pin insertion to form apertures 14 of the above-mentioned specific range of dimensions, during the pin insertion, the fibers around the pin are displaced toward the pin outlet side while the fibers are extruded radially outwardly of the direction of the pin insertion, which results in formation of the protrusions 14*e*, but with a lower height. Accordingly, at the periphery of each aperture 14, a higher-density area is formed which has a fiber density higher than that of the vicinity. With such a higher-density area, the contrast between the aperture and the periphery thereof is emphasized, so that the visibility of the apertures is advantageously improved.

(Intermediate Sheet)

For the purpose of immediately transferring the liquid permeated through the top sheet 30 to the absorber body 56, an intermediate sheet (also referred to as "second sheet") 40 may be provided, which has a higher liquid permeation rate compared to the top sheet 30. This intermediate sheet 40 is for immediately transferring the liquid to the absorber body to improve the absorption performance thereof, and to prevent the "returning" phenomenon of the absorbed liquid from the absorber body 56. The intermediate sheet 40 may be omitted.

The intermediate sheet 40 may be of a liquid-pervious sheet, such as nonwoven fabric. The intermediate sheet 40 may preferably be of air-through nonwoven fabric for its bulkiness. The air-through nonwoven fabric is preferably made of composite fibers of a core-clad structure, wherein the resin for the core may be polypropylene (PP), or preferably polyester (PET), which has a higher stiffness. The basis weight is preferably 17 to 80 g/m$^2$, more preferably 18 to 60 g/m$^2$. The fineness of the raw material fibers of the nonwoven fabric is preferably 2.0 to 10 dtex. For making nonwoven fabric bulky, it is also preferred to use eccentric fibers having off-centered cores, hollow fibers, or eccentric hollow fibers entirely as the raw material fibers or partially mixed fibers.

In the illustrated embodiment, the intermediate sheet 40 is shorter than the absorber body 56 in width and is arranged in the center, but may be provided over the entire width.

Further, the intermediate sheet 40 may be provided over the entire length of the diaper, or only in the middle portion in the front-back direction LD, including the excretion area, as in the illustrated embodiment.

(Liquid-Impervious Sheet)

The liquid-impervious sheet 11 is not particularly limited, and may preferably have moisture-permeability. As the liquid-impervious sheet 11, for example, a microporous sheet may preferably be used which is obtained by kneading an inorganic filler in a polyolefin-based resin, such as polyethylene or polypropylene, molding the kneaded mixture into a sheet, and then uni- or biaxially drawing the sheet. Alternatively, the liquid-impervious sheet 11 may be formed of nonwoven fabric as a base material, to which improved waterproof property is applied.

The liquid-impervious sheet 11 preferably extends over the same or wider extent than that of the absorber body 56 in the front-back direction LD and in the width direction WD but, when another liquid-shielding means is present, may not cover the ends or edges of the absorber body 56 in the front-back direction LD and in the width direction WD, as necessary.

(Exterior Nonwoven Sheet)

The exterior nonwoven sheet 12 covers the entire underside of the liquid-impervious sheet 11 to impart a fabric-like appearance to the product exterior. The exterior nonwoven sheet 12 preferably has a fiber basis weight of 10 to 50 g/m$^2$, in particular 15 to 30 g/m$^2$, which, however, is not limiting. The exterior nonwoven sheet 12 may be omitted, in which case the liquid-impervious sheet 11 may extend to the side edges of the product.

(Standup Gather Part)

It is preferred to provide standup gather parts 60 which stand up toward the skin of the wearer on opposed sides in the width direction WD of the top face for blocking the bodily waste moving laterally on the top sheet 30 and thereby preventing so-called side leakage. Naturally, the standup gather parts 60 may be omitted.

The standup gather parts, when employed, may be of any structure without particular limitation, and may be any of various known structures. The standup gather parts 60 in the illustrated embodiment are each composed of a gathered sheet 62 continuous substantially in the width direction WD, and elongate gathering elastic members 63 fixed in their stretched state to the gathered sheet 62 along the front-back direction LD. The gathered sheet 62 may be of water-repelling nonwoven fabric, whereas the gathering elastic members 63 may be of a rubber thread or the like. A plurality of the elastic members 63 may be provided on each lateral side as shown in FIGS. 1 and 2, or only one elastic member may be provided on each lateral side.

The inner face of the gathered sheet 62 has a joining start edge positioned on a lateral side portion of the top sheet 30 in the width direction WD, and the portion 65 outward in the width direction of this joining start edge is bonded to the inner face of the corresponding side flap SF, i.e., in the illustrate embodiment, a lateral side portion of the liquid-impervious sheet 11 and a lateral side portion of the exterior nonwoven sheet 12 located laterally outward thereof in the width direction, with a hot melt adhesive or the like.

Around each leg, each standup gather part 60 is fixed to the top sheet 30 on the center side portion 66 of the joining start edge in the width direction at both end portions 67 in the product front-back direction, while the remaining portion therebetween of the standup gather part 60 is a non-fixed free portion 68, which will be raised by the contracting force of the elastic members 63 to be brought into close contact with the body surface.

(End Flaps and Side Flaps)

The tape-type disposable diaper of the illustrated embodiment has a pair of end flaps EF, exclusive of the absorber body 56, extending respectively on the front and back sides of the absorber body 56, and a pair of side flaps SF, exclusive of the absorber body 56, extending respectively laterally beyond the opposed sides of the absorber body 56. The side flaps SF may be formed of the main body sheet (exterior nonwoven sheet 12 or the like) continuing from the portion containing the absorber body 56, or may be formed of another material and attached.

(Planar Gathers)

Each side flap SF is provided with side elastic members 64, which are of elongate elastic members, such as rubber threads, and are fixed in their stretched state in the front-back direction LD, to thereby form the round-leg portion of each side flap SF into a planar gather. The side elastic members 64 may be provided between the gathered sheet 62 and the liquid-impervious sheet 11 in the joined portion of the gathered sheet 62 in the outer vicinity in the width direction of the joining start edge as in the illustrated embodiment, or between the liquid-impervious sheet 11 and the exterior nonwoven sheet 12 in each side flap SF. A plurality of the side elastic members 64 may be provided on each lateral side as shown in the illustrated embodiment, or only one side elastic member 64 may be provided on each lateral side. Naturally, the side elastic members 64 (planar gathers) may be omitted.

The planar gathers are formed where the contracting force of the side elastic members 64 acts (in the illustrated embodiment, where the side elastic members 64 are shown). Thus, structures are conceivable, wherein the side elastic members 64 are present only in the area of the planar gathers, or wherein the side elastic members 64 are present on the front side, back side, or both of the planar gathers, but the contacting force of the side elastic members 64 acts only in the area of the planar gathers, while the contracting force is made not to act in the area other than the area of the planar gathers (substantially equivalent to absence of the elastic members) by finely cutting the side elastic members at one or a plurality of locations other than the area of the planar gathers, by not fixing the side elastic members 64 to the sheets between which the side elastic members 64 are interposed, or by both.

(Front Wings)

The present tape-type disposable diaper has front wings 80 extending on opposed sides of the product in the right-left direction at a position spaced forward of the middle of the product in the front-back direction. The front wings may be omitted (i.e., the product may be configured such that the width of the product is not varied from its narrowest portion to the front end).

The dimension of each front wing 80 in the width direction WD may suitably be decided and, for example, may be 5 to 20% (in particular 7 to 15%) the overall product length Y. The dimension of each front wing 80 in the width direction WD may be generally the same as the dimension of each back wing 81 to be discussed later in the width direction WD.

(Back Wings)

The present tape-type disposable diaper has back wings 81 extending on opposed sides of the product in the right-left direction at a position spaced backward of the middle of the product in the front-back direction.

The dimension of each back wing 81 in the width direction WD may suitably be decided and, for example, may be the same as the dimension of each front wing in the width direction WD, or smaller or larger than the dimension of the front wing in the width direction.

(Middle Section)

Each lateral edge of the product between the front wing 80 and the back wing 81 may have, for example, a generally linear portion passing the area of ±5 mm in the width direction on both sides of and in the direction orthogonal to a line at an acute angle of ±2 degrees or less with respect to the front-back direction LD. Each lateral edge of the product between the front wing 80 and the back wing 81 may extend in a wavy or arcuate manner (not shown), or in a linear manner as in the illustrated embodiment.

(Formation of Wings)

As in the illustrated embodiment, by cutting out each lateral side of the side flap SF in a concave shape, the overall concaved edge may be formed which extends from the lower edge of the front wing 80, via the lateral edge of the product between the front wing 80 and the back wing 81, to the lower edge of the back wing 81. In this case, the layered structure of the side flaps SF decides the layered structure of the front wings 80 and the back wings 81 and, in the illustrated embodiment, the front wings 80 and the back wings 81 are formed with the gathered sheet 62 and the exterior nonwoven sheet 12. Though not shown, a front extension sheet may be provided extending laterally from each side flap SF to form all or edge-side part of each front wing 80 with the front extension sheet. Similarly, a back extension sheet may be provided extending laterally from each side flap SF to form all or edge-side part of each back wing 81 with the back extension sheet. The front extension sheet and the back extension sheet may be of various nonwoven fabric.

(Connecting Part)

Each back wing 81 is provided with a connecting part 13A to be detachably connected to the ventral section F when the product is worn. That is, in fitting the product, the opposed lateral side portions of the back wings 81 are brought onto the ventral side of the wearer, and the connecting parts 13A of the back wings 81 are connected to the exterior face of the ventral section F. The connecting part 13A may be a hook member (male part) of a mechanical fastener (hook and loop fastener), or a pressure-sensitive adhesive layer. The hook member has a number of engaging projections on its connecting surface, and the engaging projections may be in various known shapes, such as tick-shaped, J-shaped, mushroom-shaped, T-shaped, or doble J-shaped (wherein J-shaped parts are joined back to back).

The connecting part 13A may directly be attached to the back wing 81, or a connecting tape 13 having the connecting part 13A may be attached to the back wing 81, as in the illustrated embodiment. The structure of the connecting tape 13 is not particularly limited and, in the illustrated embodiment, may have a tape attachment portion 13C fixed to the side flap SF, a tape body 13B protruding from the tape attachment portion 13C, and the connecting part 13A disposed in the middle of the tape body 13B in the width direction WD, and the portion beyond this connecting part 13A is a grip portion. The sheet material forming from the tape attachment portion 13C to the tape body 13B may be nonwoven fabric, plastic film, polyethylene-laminated nonwoven fabric, paper, or composites thereof.

A connecting site on the exterior face of the ventral section F to which the connecting parts 13A are to be connected, may suitably be decided, and only the body section located between the right and left front wings 80 may provide the connecting site, or the areas each extending from a lateral side portion of the body section toward the proximal side of the front wing 80 may provide the connecting site. To such connecting site, it is preferable that the connecting parts 13A may be easily connected. For example, when the connecting parts 13A are hook members (male parts) of mechanical fasteners (hook and loop fasteners), the connecting site on the exterior face of the ventral section F may be made with a loop member (female part) 24 of mechanical fasteners, or nonwoven fabric. As such a loop member 24, a plastic film stitched with a loop yarn is known, but in view of air permeability and flexibility, preferred is continuous fiber nonwoven fabric of which continuous fiber direction is its width direction WD (such as spunbonded nonwoven fabric generally having a fineness of 2.0 to 4.0 dtex, a basis weight of 20 to 50 g/m$^2$, and a thickness of 0.3 to 0.5 mm), provided with melt-bonded portions wherein fibers are melt-bonded with each other intermittently at least in the width direction WD. As in the illustrated embodiment, when a region of the exterior face of the ventral section F including the connecting site is formed with the exterior nonwoven sheet 12, the hook members may be connected to the exterior nonwoven sheet 12 without any other means added thereto. As necessary, a loop member 24 may be adhered only to the connecting site on the exterior face of the ventral section F. Further, when the connecting parts 13A are in the form of pressure-sensitive adhesive layers, a plastic film having a smooth surface to be strongly adhered to the pressure-sensitive adhesive layers may be attached to the connecting site on the exterior face of the ventral section F.

(Fixing of Top Sheet)

The top sheet 30 is preferably bonded, via a hydrophobic hot melt adhesive 31, to an underside member arranged on the underside of the top sheet 30. Instead of or in addition to this, the top sheet 30 may be joined to an underside member arranged on the underside of the top sheet 30 by melt-bonding of at least one of the top sheet 30 and the underside member arranged on the underside of the top sheet 30. The area in which the top sheet 30 is fixed may, as long as the area extends at least over the entire aperture arrayed region, only be over the aperture arrayed region or extend beyond the aperture arrayed region to other areas (e.g., all over the top sheet 30). The underside member includes the intermediate sheet 40, the wrapping sheet 58, and the liquid-impervious sheet 11 in the illustrated embodiment, but is not limited thereto.

The hydrophobic hot melt adhesive 31 may be EVA-based, polyolefin-based, or polyester/polyamide-based adhesive or the like, and a pressure-sensitive rubber-based (elastomer-based) adhesive is particularly preferred.

The amount of the hydrophobic hot melt adhesive 31 to be applied may suitably be decided, and may usually be about 0.1 to 10 g/m$^2$. In particular, with the amount of the hydrophobic hot melt adhesive 31 being about 0.5 to 5 g/m$^2$, the hot melt adhesive 31 may preferably be kept from sticking out through the apertures 14, but interference with glycerin in bonding as will be discussed later is likely to occur, so that it is preferred to combine the application amount with designing of the application pattern of the glycerin, or the like. The application pattern of the hydrophobic hot melt adhesive 31 may suitably be decided, and may preferably be a dense pattern with minute non-applied portions scattered all over (by spray application in spiral, Z, or wave shapes, or the like), or may be a continuous surface such as by slot application.

(Glycerin-Bearing Zone)

As shown in FIGS. 7, 10, and 11, the skin-touching region 30E of the top sheet 30 has glycerin-bearing zones 32 each of which bears 0.7 to 2.7 g/m$^2$ of glycerin. A glycerin-bearing zone 32 may be provided in one site with a relatively large area, or the glycerin-bearing zones 32 may be provided in a plurality of sites. The glycerin-bearing zone 32 may be provided or may not be provided, as long as it is provided at least in the skin-touching region 30E of the top sheet 30, in the other regions beyond the skin-touching region 30E.

The size, arrangement and the like of each glycerin-bearing zone 32 may suitably be decided, but it is not preferred that the size of the glycerin-bearing zone 32 is too small. Each glycerin-bearing zone 32 is preferred to have a MD (the front-back direction LD in the illustrated embodiment) dimension 32L of 5 mm or more and a CD (the width direction WD in the illustrated embodiment) dimension 32W of 5 mm or more. The MD dimension 32L of the glycerin-bearing zone 32 is more preferably 30 mm or more, further more preferably 50 mm or more, and particularly preferably 100 mm or more. The upper limit of the MD dimension 32L of the glycerin-bearing zone 32 is the overall product length Y, but may be shorter than this. The CD dimension 32W of the glycerin-bearing zone 32 is more preferably 10 mm or more. The upper limit of the CD dimension 32W of the glycerin-bearing zone 32 is the dimension in the width direction WD of the top sheet 30, but may be shorter than this.

Further, with too small area of each glycerin-bearing zone 32 with respect to the skin-touching region 30E, a moisturizer-attaching effect to the skin and the friction-reducing effect cannot be obtained sufficiently so that an area ratio of the glycerin-bearing zone 32 to the skin-touching region 30E (a total area of the glycerin-bearing zones 32/an area of the skin-touching region 30E is multiplied by 100) is preferably 3% or more, particularly preferably 5% or more. Note that since the skin-touching region 30E refers to a region exposed on the top face of the article in its spread state as discussed above, if another member serves to partly hide the top sheet 30 (in the illustrated example, the standup gather parts 60 serve to hide the opposed lateral side portions of the top sheet 30) in its spread state, the skin-touching region 30E refers to a region exposed on the top face exclusive of hidden portions of the article. On the other hand, when a whole top face of the top sheet 30 is exposed on the top face of the article, the skin-touching region 30E refers to the whole top face itself of the top sheet 30.

The glycerin-bearing zones 32 may preferably be provided in a vertical-striped pattern as in the illustrated embodiment. Alternatively, they may be provided in a horizontal-striped pattern, dotted pattern, lattice pattern. In such cases, the intervals 32X of the adjacent glycerin-bearing zones 32 may suitably be decided, and may preferably be, for example, about 1.5 to 10 mm.

The nonwoven fabric for the top sheet 30 may preferably be nonwoven fabric having a fineness of 1 to 3 dtex (more preferably 1.5 to 2.5 dtex), a basis weight of 10 to 30 g/$m^2$ (more preferably 15 to 25 g/$m^2$), and a thickness of 0.4 to 1.4 mm (more preferably 0.5 to 1.0 mm). That is, in such a nonwoven fabric, the fine fibers contribute to reducing of friction on a front face of the nonwoven fabric, which, in cooperation with the friction-reducing effect of glycerin, improves the overall friction-reducing effect. In addition, retainability of glycerin is improved by the fine fibers, to thereby further improve the friction-reducing effect. Moreover, glycerin moves from the top sheet 30 to cutis of the wearer (and in particular, penetrates through stratum corneum) so as to moisturize the cutis of the wearer (and prevent skin dryness). Therefore, a function to reduce physical irritation to the cutis of the wearer and a function to moisturize the cutis of the wearer coexist to a high degree. As a result, this nonwoven fabric has a particularly beneficial effect on the prevention of skin rash. More specifically, by the combination of the above nonwoven fabric and glycerin, the glycerin-bearing zones 32 of the top sheet 30 preferably have an average coefficient of friction MIU of 0.2 to 0.4. In addition, for forming the top sheet 30 in this context, it is particularly preferred to use discontinuous fiber nonwoven fabric.

The surface moisture percentage of the glycerin-bearing zones 32 is not particularly limited, and may preferably be 3 to 10%, particularly 4 to 8%, for moderately moistening and keeping the skin of a wearer from drying.

In order to form the glycerin-bearing zone 32, glycerin-containing hydrophilic lotion may be applied to the top sheet 30 in a desired pattern. A particularly preferred hydrophilic lotion contains 70 to 90 wt % glycerin and 10 to 30 wt % water. Such a hydrophilic lotion mainly composed of glycerin with a moderate amount of water, is preferred not only as a moisturizer when transferred to the skin, but also for its hardness to decay as the water is held in the glycerin as bound water (glycerin has an extremely high water retainability). That is, for using a water-containing hydrophilic lotion in this context, it is preferred to contain a large amount of glycerin, to ensure a sufficient surface moisture percentage (e.g., 3 to 10% as discussed above), and to keep a water activity value of the hydrophilic lotion low, for example, 0.8 or lower, more preferably 0.3 to 0.7, particularly preferably 0.3 to 0.5, so that, even in the absence of a preservative, development of microorganisms may be suppressed to provide improved shelf life, and the moisturizing effect upon transfer to the skin may be improved.

The hydrophilic lotion can contain one or more kinds additives selected from the group of emulsifier, phosphate ester, paraffin and surfactant. Preferable surfactant is nonionic surfactant including an ether type nonionic surfactant and an EO-PO type nonionic surfactant. For improved product shelf life, the hydrophilic lotion may contain a preservative but, as the hydrophilic lotion is to be transferred to the skin for moistening the same, it is more preferred that the hydrophilic lotion is free of preservatives.

The content of glycerin in the glycerin-bearing zone 32 may be suitably decided within a range of 0.7 to 2.7 g/$m^2$, and more preferably within a range of 1.0 to 2.2 g/$m^2$. As an example, for forming the glycerin-bearing zone 32 by applying the hydrophilic lotion, which contains 70 to 90 wt % glycerin and 10 to 30 wt % water, to the top sheet 30, the application amount of the hydrophilic lotion in the glycerin-bearing zone 32 may be about 5 to 15 g/$m^2$. When a plurality of zones 32*a*, 32*b* with different contents of the hydrophilic lotion is present as in the embodiment shown in FIG. 11, or when the applied amount of the hydrophilic lotion varies gradually, as long as a portion with the content of glycerin within the above prescribed range is present in such glycerin-bearing zone 32, the content of glycerin all over the glycerin-bearing zone 32 may be less than or more than the above prescribed range.

The content of glycerin is measured by the following measurement method.

(Method for Measuring Content of Glycerin)

The four identical products are provided. In one product arbitrarily selected from these four products, the size of the glycerin-bearing zone 32 is measured by a method to be discussed later so as to obtain an area of the glycerin-bearing zone 32 (when a plurality of glycerin-bearing zones 32 is present, the area refers to a total area thereof).

All the glycerin-bearing zones 32 are cut out from the four top sheets 30 of the four identical products, respectively (In each of the top sheets 30, a cut piece is unnecessary to be limited to the glycerin-bearing zone 32 by cutting precisely along the peripheral edge thereof. That is, as long as the glycerin-bearing zone 32 is included in each cut piece, in addition to the glycerin-bearing zone 32, surrounding thereof may be also included to some degree.) Thus these glycerin-bearing zones 32 are used as the test pieces. Alternatively, from the four identical products, the four top sheets 30 are peeled off, which are as they are directly used as the test pieces.

The test pieces are put into water having a temperature of 25° C. contained in a 300 ml beaker where the test pieces are picked randomly or stirred with a glass rod for 1 minute or more. After that, the beaker is left to stand for 60 minutes in a state where the test pieces are immersed in water. While the beaker is left to stand, to keep a height of position of test pieces as low as possible, the four test pieces are folded up and a weight is put on the folded test pieces, alternatively, the four test pieces are previously folded up and fixed to each another by means of adhesive bonding or stitching. The volume of water contained in the beaker is to be the lowest (for example, 10 ml) in a range wherein the folded test pieces can be totally immersed in water. After the above being left to stand, the test pieces are picked randomly or stirred with the glass rod for 1 minute or more, lifted from the water, and then, squeezed sufficiently. A concentration of glycerin in glycerin-containing water thus remained in the beaker is measured with a glycerin concentration meter and also a weight of the remained glycerin-containing water is measured. Based on these measurement results, a weight of the glycerin in the glycerin-containing water is obtained.

Finally, the weight of the glycerin in the glycerin-containing water is divided with a value obtained by multiplying an area of glycerin-bearing zone with four (because of four products) such that a content (g/m$^2$) of the glycerin in the glycerin-bearing zone 32 is calculated.

The nonwoven fabric for the top sheet 30 is preferably formed of hydrophobic resin fibers for their low cost, which as they are have poor retainability of glycerin for using the water-containing hydrophilic lotion. Thus, the hydrophilic lotion preferably has a viscosity at 20° C. of 150 to 400 mPa-s. In this way, the glycerin-retainability of the nonwoven fabric is improved advantageously.

Because of the same reason, the nonwoven fabric for the top sheet 30 is preferably formed of hydrophilized fibers wherein hydrophobic resin fibers have been coated with a hydrophilizer. In this way, the glycerin-retainability of the nonwoven fabric is improved advantageously.

The hydrophilizer may preferably be, in consideration of safety for human body, safety in process, or the like factors, one or a mixture of nonionic activators obtained by addition of ethylene oxide to higher alcohols, higher fatty acids, alkylphenols, or the like, or anionic activators, such as alkyl phosphates (octyl or dodecyl) or alkyl sulfates. The amount to be applied may vary depending on the required performance, but may usually preferably be about 0.1 to 2.0 wt %, particularly about 0.2 to 1.0 wt % of the dry weight of the objective sheet.

<Efficacy Test of Sensory Evaluation>

Various samples of the top sheet as specified in Tables 1 to 3 were subjected to determination of various properties, including average coefficient of friction MIU, surface moisture percentage, and water activity value. The content of glycerin was measured by the measuring method as discussed above. Samples 1 to 10 were nonwoven fabric before fabrication into products, to which the hydrophilic lotion was or was not applied, and Samples 11 to 15 were top sheets removed from commercial products. Further, smoothness and moistness of each sample were perceived by stroking the top face of the top sheet in the longitudinal direction with the hand, and graded on three heights with respect to those of Sample 5 (◎: excellent; Δ: better than Sample 5; x: similar)

TABLE 1

| Sample number | | 1 | 2 | 3 | 4 | 5 |
|---|---|---|---|---|---|---|
| Top sheet | Fineness (dtex) | 2.0 (PE)/ 2.2 (PET) | 2.0(PE)/ 2.2 (PET) | 2.0(PE)/ 2.2 (PET) | 2.0 (PE)/ 2.2 (PET) | 2.0 (PE)/ 2.2 (PET) |
| | Basis weight (g/m$^2$) | 25 | 20 | 20 | 20 | 20 |
| | Thickness (mm) | 1.1 | 0.9 | 0.9 | 0.6 | 0.6 |
| | Material of fiber | PE/PET (mixed) | PE/PET (mixed) | PE/PET (mixed) | PE/PET (mixed) | PE/PET (mixed) |
| | Fiber joining | thermal bonding | thermal bonding | thermal bonding | thermal bonding | thermal bonding |
| Glycerin-bearing zone | Arrangement | vertical-striped | vertical-striped | vertical-striped | vertical-striped | — |
| | MD dimension (mm) | 200 | 200 | 200 | 200 | — |
| | CD dimension (mm) | 5 | 5 | 5 | 5 | — |
| | Number (Interval 32x) | 4 (5) | 4 (5) | 4 (10) | 4 (5) | — |
| Content of glycerin | (g/m$^2$) | 1.7 | 1.3 | 1.4 | 1.1 | 0 |
| Lotion composition (wt %) | Glycerin | 76 | 76 | 76 | 76 | — |
| | Liquid paraffin | 2 | 2 | 2 | 2 | — |
| | Alkyl phosphate | 2 | 2 | 2 | 2 | — |
| | Water | 20 | 20 | 20 | 20 | — |
| Application amount of lotion | (g/m$^2$) | 8.5 | 8.5 | 8.5 | 8.5 | 0 |
| Lotion viscosity (mPa · s) 20° C. | | 372 | 372 | 372 | 372 | — |
| Average coefficient of friction MIU | | 0.33 | 0.34 | 0.34 | 0.33 | 0.37 |
| Variation deviation of average coefficient of friction MMD | | 0.01 | 0.01 | 0.01 | 0.01 | 0.01 |
| Surface moisture percentage (%) | | 5.6 | 5.6 | 5.6 | 5.6 | 0.3 |
| Smoothness | | ⊙ | ⊙ | ⊙ | ⊙ | — |
| Moistness | | ⊙ | ⊙ | ⊙ | ⊙ | — |

TABLE 2

| Sample number | | 6 | 7 | 8 | 9 | 10 |
|---|---|---|---|---|---|---|
| Top sheet | Fineness (dtex) | 2.0(PE)/ 2.2 (PET) | 2.0(PE)/ 2.2 (PET) | 2.0 (PE)/ 2.2 (PET) | 2.0 (PE)/ 2.2 (PET) | 2.2(PE)/ 3.3 (PET) |
| | Basis weight ($g/m^2$) | 20 | 20 | 20 | 20 | 20 |
| | Thickness (mm) | 0.6 | 0.6 | 0.6 | 0.6 | 0.6 |
| | Material of fiber | PE/PET (mixed) | PE/PET (mixed) | PE/PET (mixed) | PE/PET (mixed) | PE/PET 2-layered |
| | Fiber joining | thermal bonding | thermal bonding | thermal bonding | thermal bonding | thermal bonding |
| Glycerin-bearing zone | Arrangement | vertical-striped | vertical-striped | vertical-striped | vertical-striped | vertical-striped |
| | MD dimension (mm) | 200 | 200 | 200 | 200 | 200 |
| | CD dimension (mm) | 5 | 5 | 5 | 5 | 5 |
| | Number (Interval 32x) | 4 (5) | 4 (5) | 4 (5) | 4 (5) | 4 (5) |
| Content of glycerin | ($g/m^2$) | 0.50 | 0.70 | 2.6 | 2.8 | 1.2 |
| Lotion composition (wt %) | Glycerin | 76 | 76 | 76 | 76 | 76 |
| | Liquid paraffin | 2 | 2 | 2 | 2 | 2 |
| | Alkyl phosphate | 2 | 2 | 2 | 2 | 2 |
| | Water | 20 | 20 | 20 | 20 | 20 |
| Application amount of lotion | ($g/m^2$) | 3.5 | 5.0 | 15.0 | 17.6 | 8.5 |
| Lotion viscosity (mPa · s) 20° C. | | 372 | 372 | 372 | 372 | 372 |
| Average coefficient of friction MIU | | 0.41 | 0.40 | 0.30 | 0.30 | 0.51 |
| Variation deviation of average coefficient of friction MMD | | 0.01 | 0.01 | 0.01 | 0.01 | 0.01 |
| Surface moisture percentage (%) | | 3.0 | 4.2 | 8.0 | 8.9 | 3.0 |
| Smoothness | | ○ | ○ | ⊙ | ⊙ | Δ |
| Moistness | | ○ | ○ | ⊙ | ⊙ | Δ |

TABLE 3

| Sample number | | 11 | 12 | 13 | 14 | 15 |
|---|---|---|---|---|---|---|
| Top sheet | Fineness (dtex) | Company A | Company B | Company A | Company B | Company C |
| | Basis weight ($g/m^2$) | Commercial 1 diaper | Commercial 1 diaper | Commercial 1 diaper | Commercial 1 diaper | Commercial 1 diaper |
| | Thickness (mm) | 1 | 1 | 2 | 2 | |
| | Material of fiber | | | | | |
| | Fiber joining | | | | | |
| Glycerin-bearing zone | Arrangement | — | — | — | — | — |
| | MD dimension (mm) | — | — | — | — | — |
| | CD dimension (mm) | — | — | — | — | — |
| | Number (Interval 32x) | — | — | — | — | — |

TABLE 3-continued

| Sample number | | 11 | 12 | 13 | 14 | 15 |
|---|---|---|---|---|---|---|
| Content of glycerin | ($g/m^2$) | — | — | — | — | — |
| Lotion composition (wt %) | Glycerin | — | — | — | — | — |
| | Liquid paraffin | — | — | — | — | — |
| | Alkyl phosphate | — | — | — | — | — |
| | Water | — | — | — | — | — |
| Application amount of lotion | ($g/m^2$) | — | — | — | — | — |
| Lotion viscosity (mPa · s) 20° C. | | — | — | — | — | — |
| Average coefficient of friction MIU | | 0.65 | 0.62 | 0.48 | 0.69 | 0.58 |
| Variation deviation of average coefficient of friction MMD | | 0.01 | 0.01 | 0.01 | 0.01 | 0.01 |
| Surface moisture percentage (%) | | 0.3 | 0.1 | 0.2 | 0.3 | 0.3 |
| Smoothness | | x | x | Δ | x | x |
| Moistness | | x | x | x | x | x |

As may be seen from Tables 1 to 3, it was revealed that the top face of the top sheets of Samples 1 to 4 and 6 to 9, in particular Samples 1 to 4, 8, and 9, were perceived as being very smooth and moist. Compared to these, Samples 10 to 15 were inferior in smoothness and moistness. Sample 9 was moist but provided sticky feel.

<Measurement of Transepidermal Water Loss (TEWL) and Measurement of Stratum Corneum Water Content>

After bringing cutis of human subjects (two males and one female in their thirties) into contact with the top sheets for one hour, respectively, the transepidermal water loss (TEWL) and the stratum corneum water content were measured in the following procedures (1) to (6). For the measurement of transepidermal water loss (TEWL), VapoMeter SWL-5001 manufactured by Delfin Technologies Ltd. was used as a portable water loss meter, whereas for the measurement of the stratum corneum water content, Skin Surface Hygrometer SKICON-200EX-USB manufactured by YAYOI CO., LTD. was used as a device for measuring the stratum corneum water content.

(1) The top sheet of Sample 1 shown in Table 1, the top sheet of Sample 11 shown in Table 3, the top sheet of Sample 14 shown in Table 3, and the top sheet of Sample 15 shown in Table 3 were cut to form 2 cm square test pieces, respectively. As for each test piece of Sample 1, note that the top sheet of Sample 1 was cut such that a glycerin-bearing zone is disposed so as to pass through a center of the test piece.

(2) Four measurement points were marked at 8 cm, 11 cm, 14 cm, and 17 cm above a wrist of each arm of all human subjects (in total, eight measurement points for each human subject and twenty four measurement points for all human subjects).

(3) About 0.1 g of fluff pulp was left to stand at each measurement point of each human subject and 1 ml of alkali aqueous (0.1M $Na_2CO_3$ (aq)) was dropped to the fluff pulp.

Then, the arm was wrapped at each measurement point with food wrap film which covers the fluff pulp from above such that the fluff pulp is fixed thereto. The wrapped arm was left for one hour as it was.

(4) Then after this leaving for one hour, the food wrap film and the fluff pulp were removed such that the exposed measuring point was wiped gently with a rag formed of paper for experiments.

(5) The wiped measurement point was dried for 15 minuets, and then, the test piece was placed on the measurement point and fixed thereto with cellulose adhesive tape. The measurement point to which the test piece was fixed was left for one hour as it was.

(6) Then after this leaving for one hour, the test piece was removed. TEWL was measured three times at each measurement point and the average of all measured values of all human subjects was taken as the result of measurements of TEWL for each sample. After the measurements of TEWL, the stratum corneum water content was measured three times at each measurement point and the average of all measured values of all human subjects was taken as the result of measurements of stratum corneum water content for each sample.

As for the stratum corneum water content, FIG. 13 shows a graph for comparing the results of the measurements for the four samples. In addition, as for TEWL, FIG. 14 shows a graph for comparing the results of the measurements for the four samples. As may be seen from these results of the measurements, it was revealed that when the (glycerin-bearing) top sheet of Sample 1 including the glycerin-bearing zone was used, comparing with other top sheets bearing no glycerin, moisture of the skin was hard to be escaped outside and the skin was moisturized sufficiently.

<Observation Test of Cutis by Doctor>

Diaper samples were prepared each having the substantially same structure as that of a tape-type disposable diaper illustrated in FIGS. 1 to 5 and 10 and being provided with the (glycerin-bearing) top sheet of Sample 1 shown in Table 1. Then, human subjects used continuously the diaper samples for one week. A doctor observed cutis conditions of these human subjects right before and right after they used the diaper samples. Note that the human subjects were thirty three healthy infants being from six months to one year old and they had usually used tape-type disposable diapers (provided with top sheets bearing no glycerin).

As a result, from finding in the observations by the doctor, problematic symptoms were not found after the observation tests. Further, although there had been seven infants having erythema before the observation tests, improvement tendencies were confirmed as for six infants among the seven infants after the observation tests.

<Measurement of Amount of IL-1α Secretion>

Using a three-dimensional cultured skin model (immature model), an action of the top sheet on the production of IL-1α was evaluated as discussed below.

SkinEthic RHE-D7 (provided by EPISKIN, Inc. hereinafter referred to as RHE) was used as the three-dimensional cultured skin model. RHE was cultured for two hours in a 24-well plate to be conditioned, using Growth Medium (provided by EPISKIN, Inc).

A top sheet similar to the top sheet of Sample 1 shown in Table 1 was provided. The top sheet was cut according to a surface shape of RHE (that is, circular shape with a diameter of 8 mm) into a blank test piece. Then, hydrophilic lotion having the same amount and the same composition as those of hydrophilic lotion for Sample 1 shown in Table 1 was applied to a whole surface of the blank test piece for obtaining a glycerin-bearing test piece.

The test piece was directly placed on a top face of the conditioned RHE to be acclimated thereto such that incubation was performed for 72 hours. In this incubation, when the first 24 hours had passed since the test piece was placed on RHE, the test piece was removed. Then, Growth Medium was replaced with flesh Growth Medium and successive culture was performed with a fresh test piece. The culture medium was collected such that an amount of IL-1α secretion on DAY 1 (the first day) was measured with an ELISA method. Further, when the next 24 hours had passed (in total, after 48 hours), the test piece was removed. Then, Growth Medium was replaced with flesh Growth Medium and successive culture was performed with a flesh test piece. The culture medium was collected and an amount of IL-1α secretion on DAY 2 (the second day) was measured in the same operation as in DAY 1. Finally, when the last 24 hours had passed (in total, after 72 hours), the test piece was removed. Then, the culture medium was collected and an amount of IL-la secretion on DAY 3 (the third day) was measured in the same operation as in DAY 1. Note that RHE was collected to be used for a measurement of amount of filaggrin as will be discussed later.

Similarly, also in a case (control) where nothing was placed on the top face of RHE, an amount of IL-1α secretion was measured and RHE was collected.

The amount of IL-1α secretion was measured on each of DAY 1 to DAY 3 by quantitating the amount of IL-1α secretion in the culture medium with the sandwich ELISA method in which anti-IL-1α antibody Human IL-1α/IL-1F1 Antibody MAB200 (provided by R&D SYSTEMS, Inc.) diluted to the appropriate concentration was used as a capture antibody and biotin-labeled anti-IL-1α antibody Human IL-la/IL-1F1 Biotinylated Antibody BAF 200 (provided by R&D SYSTEMS, Inc.) was used as a detector antibody. A detailed procedure is as follows. That is, the collected medium diluted to the predetermined concentration was added to a plate coated with the capture antibody for allowing incubation and then, the detector antibody was added. Further, Streptavidin-HRP DY998 (provided by R&D SYSTEMS, Inc.) was added thereto to take place reaction and substrate solution Substrate Reagent Pack DY999 (provided by R&D SYSTEMS, Inc.) was added thereto to take place reaction. Eventually, Stop Solution DY994 (provided by R&D SYSTEMS, Inc.) was added to stop the reaction and absorbance at 450 nm was measured.

As for a total amount of secretion of IL-1α on DAY 1 to DAY 3, as shown in FIG. 15, in a case of the glycerin-bearing test piece, the amount is 4.7±7.5 (pg/model), which is less than half of the amount being 10.5±4.9 (pg/model) in a case of the blank test piece. Note that when the amount of IL-1α is below a detection limit, the amount is assumed to be zero.

<Measurement of Amount of Filaggrin>

Using a three-dimensional cultured skin model (immature model), an action of the top sheet on the amount of filaggrin was evaluated as stated below.

From a frozen block where the RHE collected in each measurement of amount of IL-1α secretion was embedded in OCT compound, a section having a thickness of 5 μm was prepared. With respect to the section adhered to a glass slide and air dried, 4% Paraformaldehyde in PBS (−) was added thereto for immobilization at room temperature for 15 minutes and 1% bovine serum albumin (BSA) in PBS (−) was added thereto for blocking at room temperature for one hour. After that, the reaction of Anti-Filaggrin Antibody (provided by Gene Tex, Inc.) was taken place at 40° C. for one night. Then, the reaction of Anti-mouse IgG Alexa Fluor 488 (provided by Cell Signaling Technology, Inc.) as the secondary antibody was taken place at room temperature for two hours. The obtained cell nucleus was stained using Hoechst 33342 (provided by Cell Signaling Technologies, Inc.) as counterstain and mounted with Marinol (provided MUTO PURE CHEMICALS CO., LTD.) Thus, emitting of green fluorescence (filaggrin) and emitting of blue fluorescence (nuclei of cells) were observed with a fluorescence microscope.

As a result of the observation, as shown in FIG. 16, in a case of the control, expression of filaggrin was observed in full-thickness of the stratum corneum. In a case of the blank test piece placed on the top face of the stratum corneum, the expression of filaggrin is decreased comparing with the case of control. On the other hand, in a case of the glycerin-bearing test piece placed on the top face of the stratum corneum, decrease of the expression of filaggrin was inhibited comparing with the case of the blank test piece placed thereon.

Description of Terms Used in Specification

The following terms appearing in the present specification shall have the following means unless otherwise specified herein.

The "front-back direction" refers to the direction shown by the reference sign LD (longitudinal direction) in the figures, whereas the "width direction" refers to the direction shown by the reference sign WD (right-left direction) in the figures, and the front-back direction and the width direction are orthogonal to each other.

The "machine direction (MD)" and "cross direction (CD)" refer to the flow direction (MD) and the lateral direction orthogonal thereto (CD) in the production facilities, respectively, and either one of these is aligned to the front-back direction while the other is aligned to the width direction, depending on the parts of the product. The MD of nonwoven fabric is the direction of fiber orientation in the nonwoven fabric. The fiber orientation refers to the direction along which the fibers of the nonwoven fabric are aligned, and may be identified, for example, by a measurement method pursuant to the fiber orientation testing method using zero-span tensile strength prescribed in TAPPI Standard Method T481, or by a simplified measurement method for determining the fiber orientation by the ratio of tensile strengths in the front-back direction and in the width direction.

The “top side” refers to the side, when the article is worn, closer to the skin of the wearer, whereas the “underside” refers to the side, when the article is worn, away from the skin of the wearer.

The “top face” refers to the face, when the article is worn, closer to the skin of the wearer, whereas the “under face” refers to the face, when the article is worn, away from the skin of the wearer.

The “area ratio” refers to the ratio of the objective area per unit area, and is calculated by dividing the sum of the areas of objective portions (e.g., apertures) in an objective region (e.g., cover nonwoven sheet) by the area of that objective region, and is represented in percentage. In a configuration where a number of objective portions are provided at intervals, the area ratio is preferably determined with the objective region being set to a size containing 10 or more objective portions. For example, the area ratio of the apertures may be determined in the following procedure, using, for example, VHX-1000 (trade name) manufactured by KEYENCE under the measurement conditions in ×200 magnification.

(1) Place a specimen under a ×20 magnification lens, and adjust the focus. Position the nonwoven fabric so that 4×6 apertures are in the field.

(2) Specify the brightness of the pore portions, and measure the area of the holes.

(3) Click the color extraction in “Area Measurement” under “Measurement and Comment”. Click the pore portions.

(4) Click “collective Measurement”, check “Display measurement result window”, and store in CSV data.

The “stretch rate” refers to a value with respect to the natural length being 100%. For example, a 200% stretch rate is synonymous with stretch in two folds.

The “gel strength” is determined as follows. To 49.0 g of artificial urine (a mixture of 2 wt % urea, 0.8 wt % sodium chloride, 0.03 wt % calcium chloride dihydrate, 0.08 wt % magnesium sulfate heptahydrate, and 97.09 wt % ion-exchanged water), 1.0 g of superabsorbent polymer is added and stirred with a stirrer. The resulting gel is left in a chamber with constant temperature and humidity at 40° C. at 60% RH for 3 hours, and then the temperature is returned to the ordinary temperature. The gel strength is measured in a curd meter (Curdmeter-MAX ME-500 manufactured by I. techno Engineering).

The “basis weight” is determined as follows. A specimen or test piece is preliminarily dried, left in a laboratory or in apparatus under the standard conditions (23±1° C. temperature and 50±2% relative humidity in the testing location) until constant mass is attained. The preliminary drying refers to attaining constant mass from a specimen or test piece in the environment at a temperature of 100° C. No preliminary drying may be performed on fibers with an official regain of 0.0%. From the test piece of the constant mass, a specimen of 100 mm×100 mm size is cut out using a sampling template (100 mm×100 mm). The weight of the specimen is measured and multiplied by 100 times to calculate the weight per 1 $m^2$, which is taken as the basis weight.

The “thickness” is automatically measured using an automatic thickness meter (KES-G5 handy compression tester program) under a load of 0.098 $N/cm^2$ with the compression area of 2 $cm^2$. The thickness of perforated nonwoven fabric is measured at a position other than the apertures and the protrusions therearound.

The water absorption is determined in accordance with JIS K7223-1996 “Testing method for water absorption capacity of super absorbent polymers”.

The water absorption rate is defined as the “time spent until the end point is reached” in carrying out JIS K7224-1996 “Testing method for water absorption rate of super absorbent polymers” using 2 g of superabsorbent polymer and 50 g of saline.

The “spread state” refers to the state in which an article is spread flatly without contraction or slack.

The size of each part refers to the size not in the natural length state but in the state where, unless otherwise specified.

The “melt viscosity” is determined at a prescribed temperature using a Brookfield B-type viscometer (spindle No. 027) in accordance with JIS Z 8803.

The “maximum dimension” of an aperture refers to the longer of the MD dimension and the CD dimension.

When “glycerin-bearing zone” can be identified visually because of coloring or the like, the size of the glycerin-bearing zone can be measured based on the identified shape thereof. On the other hand, the “glycerin-bearing zone”, if cannot be identified visually, may be identified through appropriate measures.

For example, a necessary number of specimens (for measurement and for positional identification) are provided, which have the glycerin-bearing zones 32 at the same positions, the glycerin-bearing zones 32 on the top sheet 30 of a specimen for positional identification are colored with an appropriate coloring agent in a color different from that of the surroundings, the colored areas are identified using a ruler or other proper image measurement device, and then the measurement is made on a specimen for measurement at the same positions as those of the colored areas identified in the specimen for positional identification, which positions are regarded as the glycerin-bearing zones 32. For coloring the glycerin-bearing zones 32, a water leak testing agent MORAYMILLE W manufactured by TASETO CO., LTD. may preferably be used.

In addition, when the water content of glycerin-bearing zone 32 reaches a certain level or more, an image of the top face of the top sheet is taken with Near-infrared Ray Camera NIRCam-640 SN manufactured by Vision Sensing Co., Ltd. under illumination (light in the room and outside light through the window). As a result, the glycerin-bearing zone 32 can be visualized (identified), due to the different color of the glycerin-bearing zone 32 from those of the surroundings. Thus, the size of the glycerin-bearing zone 32 can be measured.

The “average coefficient of friction MIU” and the “variation deviation of average coefficient of friction MMD” is determined using a friction tester KES-SE manufactured by KATO TECH CO., LTD. (10 mm square silicon sensor, 50 g load), and refers to the value measured for the sensor moving distance of 20 mm. The sensor moving direction (direction of friction) is the MD of the top sheet. When a product is to be subjected to the measurement, members constituting the product except for the top sheet are removed or cut out to the extent that the friction test on the top sheet surface would not be affected (as such, members, for example, melt-bonded to the top sheet will not be removed), and the test is conducted on the top sheet in its spread state.

In addition, when the CD dimension of a glycerin-bearing zone on the top sheet is less than the sensor dimension (10 mm), the top sheet 30 is cut along the lateral edges of the glycerin-bearing zone 32 as shown in FIG. 12(*a*) to obtain a specimen 300 solely of the glycerin-bearing zone 32 (narrower in width than the sensor 100), and this specimen is subjected to measurement with the center of the sensor 100 being aligned to the center of the specimen 300 in the CD as shown in FIG. 12(*b*). In every measurement, glycerin remaining on the surface of the sensor 100 is thoroughly wiped off before next measurement.

Note that the glycerin-bearing zone 32 is identified by the above mentioned method.

The "surface moisture percentage" is an average calculated from the values measured at three arbitrary positions in the glycerin-bearing zones 32 using a moisture checker MY-808S manufactured by SCALAR CORPORATION. Note that in every measurement, glycerin and the like remaining on the measuring surface of the moisture checker is thoroughly wiped off before next measurement. Note that the glycerin-bearing zone 32 is identified by the above mentioned method.

The "water activity value" may be determined using an electric resistance-type water activity meter, such as EZ-100 ST (electric resistance type) manufactured by FREUND CORPORATION. Before measurement, calibration is performed with a saturated solution. Measurement may be made according to an electric resistance-type test based on Standard Methods of Analysis in Food Safety Regulation. Specifically, a sample is taken in a volume of 3% or more the inner capacity of the detector of the water activity meter, placed on an aluminum foil dish or an open flat plate, immediately introduced into and sealed in the detector, and subjected to the conditions of 25±2° C. The values are read every 10 minutes and, when fluctuation of the value is no longer observed, the water vapor pressure in the detector is regarded as in equilibrium, and the value at that point is taken as the measured value of that sample. Each sample is measured three times, and the average of the three measured values is taken as the water activity value.

The "viscosity" is determined at a prescribed temperature using a Brookfield B-type viscometer (spindle No. 027) in accordance with JIS Z 8803.

A test or measurement shall be, in the absence of description about environmental conditions, performed in a laboratory or in apparatus under the standard conditions (23±1° C. temperature and 50±2% relative humidity in the testing location).

INDUSTRIAL APPLICABILITY

The present invention is applicable not only to underpants-type disposable diapers or tape-type disposable diapers, but also to general disposable wearable articles, such as pad-type disposable diapers, disposable swim wears, diaper covers, or sanitary napkins.

REFERENCE SIGN LIST

11: liquid-impermeable sheet
12: exterior nonwoven sheet
14: aperture
14*e*: protrusion
30: top sheet
30E: skin-touching region
31: hydrophobic hot melt adhesive
32: glycerin-bearing zone
40: intermediate sheet
50: absorbent element
56: absorber body
58: wrapping sheet
60: standup gather part
62: gathered sheet
90: group
93: imperforated zone
94: unit arrayed area
LD: front-back direction
WD: width direction

The invention claimed is:

1. A disposable wearable article comprising a top sheet having a skin-touching region that is brought into contact with skin of a wearer, wherein the top sheet is made from discontinuous fiber nonwoven fabric having a fineness of 1 to 3 dtex, a basis weight of 10 to 30 g/$m^2$, and a thickness of 0.5 to 1.4 mm, wherein the skin-touching region has a glycerin-bearing zone to which a hydrophilic lotion containing 70 to 90 wt % glycerin and 10 to 30 wt % water is applied, wherein the hydrophilic lotion has a viscosity at 20° C. of 150 to 400 mPa·s, wherein the glycerin-bearing zone comprises a zone bearing 0.7 to 2.7 g/$m^2$ of glycerin and having a Machine Direction dimension of 5 mm or more and a Cross Direction dimension of 5 mm or more, and wherein an area ratio of the glycerin-bearing zone to the skin-touching region is 3% or more.

2. The disposable wearable article according to claim 1, wherein an amount of IL-Ica secretion measured by bringing the glycerin-bearing zone of the top sheet into contact with a three-dimensional cultured skin model is one-half or less of that measured in a case of another sheet being different from the top sheet only in that the other sheet does not bear glycerin.

3. The disposable wearable article according to claim 2, wherein an amount of filaggrin measured by bringing the glycerin-bearing zone of the top sheet into contact with a three-dimensional cultured skin model is larger than that measured in a case of another sheet being different from the top sheet only in that the other sheet does not bear the glycerin.

4. The disposable wearable article according to claim 2, wherein the nonwoven fabric is nonwoven fabric formed of hydrophilized fibers in which hydrophobic resin fibers have been coated with a hydrophilizer.

5. The disposable wearable article according to claim 1, wherein an amount of filaggrin measured by bringing the glycerin-bearing zone of the top sheet into contact with a three-dimensional cultured skin model is larger than that measured in a case of another sheet being different from the top sheet only in that the other sheet does not bear the glycerin.

6. The disposable wearable article according to claim 5, wherein the nonwoven fabric is nonwoven fabric formed of hydrophilized fibers in which hydrophobic resin fibers have been coated with a hydrophilizer.

7. The disposable wearable article according to claim 1, wherein the nonwoven fabric is nonwoven fabric formed of hydrophilized fibers in which hydrophobic resin fibers have been coated with a hydrophilizer.

8. The disposable wearable article according to claim 1, wherein the glycerin-bearing zone includes a plurality of zones with different contents of glycerin, wherein the plurality of zones are connected in a front-back direction and extending along the front-back direction over an entirety of the article.

* * * * *